US011841317B2

(12) United States Patent
Flammiger

(10) Patent No.: US 11,841,317 B2
(45) Date of Patent: Dec. 12, 2023

(54) DEVICE AND PROCESS FOR DETECTING A GAS, ESPECIALLY A HYDROCARBON

(71) Applicant: Dräger Safety AG & Co. KGaA, Lübeck (DE)

(72) Inventor: Andreas Flammiger, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 17/518,946

(22) Filed: Nov. 4, 2021

(65) Prior Publication Data

US 2022/0146410 A1 May 12, 2022

(30) Foreign Application Priority Data

Nov. 12, 2020 (DE) ................. 10 2020 129 858.7

(51) Int. Cl.
*G01N 21/31* (2006.01)
*G01N 33/00* (2006.01)

(52) U.S. Cl.
CPC ......... *G01N 21/31* (2013.01); *G01N 33/0047* (2013.01)

(58) Field of Classification Search
None
See application file for complete search history.

(56) References Cited

U.S. PATENT DOCUMENTS 5,693,945 A * 12/1997 Akiyama ............... G01N 21/33
250/343
5,721,430 A * 2/1998 Wong ................. G01N 21/3518
250/338.5
6,583,417 B2 * 6/2003 Stock ................... G01N 21/314
250/338.5
6,818,895 B2 * 11/2004 Williams ........... G01N 21/3504
250/343
2003/0205673 A1 11/2003 Williams
2004/0104345 A1 6/2004 Kansakoski et al.
2010/0078563 A1 4/2010 Haver et al.
(Continued)

FOREIGN PATENT DOCUMENTS

DE 202011102765 U1 8/2012
DE 102012007561 A1 10/2013
(Continued)

*Primary Examiner* — Tarifur R Chowdhury
*Assistant Examiner* — Roberto Fabian, Jr.
(74) *Attorney, Agent, or Firm* — McGlew and Tuttle, P.C.

(57) ABSTRACT

A gas detection device and process detect a target gas for monitoring an area for the target gas. A radiation source emits electromagnetic radiation (50) that penetrates the area and impinges on an array of filters (15, 25) that distributes the impinging radiation (50) onto a first gas photosensor (35), a second gas photosensor (37) and a reference photosensor (36). The first gas photosensor (35) is only sensitive to radiation in a first wavelength range, the second gas photosensor (37) is only sensitive to radiation in a second wavelength range and the reference photosensor (36) is only sensitive to radiation in a reference wavelength range. The wavelength ranges are spaced apart from one another. An analysis unit (10) analyzes signals [Sig(35), Sig(36), Sig (37)] from the three photosensors (35, 36, 37) and carries out three pair comparisons to determine whether or not the target gas is present.

21 Claims, 12 Drawing Sheets

(56) References Cited

U.S. PATENT DOCUMENTS

2014/0361172 A1* 12/2014 Little, III ............. G01N 21/359
                                                              250/339.06
2016/0231244 A1*  8/2016 Camargo ............... G01N 21/61
2016/0349228 A1* 12/2016 Kester ................... G01J 5/0014
2018/0313749 A1* 11/2018 Enquist ............. G01N 33/0026

FOREIGN PATENT DOCUMENTS

| DE | 102016108544 A1 | 11/2017 |
| WO | 2012099924 A1 | 7/2012 |
| WO | 2014113287 A1 | 7/2014 |

* cited by examiner

DEVICE AND PROCESS FOR DETECTING A GAS, ESPECIALLY A HYDROCARBON

CROSS REFERENCE TO RELATED APPLICATIONS

This application claims the benefit of priority under 35 U.S.C. § 119 of German Application 10 2020 129 858.7, filed Nov. 12, 2020, the entire contents of which are incorporated herein by reference.

TECHNICAL FIELD

The present invention pertains to a gas detection device for detecting a gas in an area to be monitored, wherein the gas detection device comprises a plurality of photosensors and an array of filters. The present invention pertains, furthermore, to a process for monitoring an area for a gas using such a gas detection device. The gas to be detected is often also called "target gas."

TECHNICAL BACKGROUND

The usually adverse event that an explosive gas, especially methane or another gas with short-chain alkanes, or a toxic gas is being released in a refinery or another production plant or warehouse or transport vehicle must be detected. The event that an explosive or toxic gas has been released has to be detected rapidly and reliably in order to be able to trigger a suitable action immediately and hence especially to avoid an explosion or a fire or a poisoning of a living being.

A photoelectrically operating gas detection device is often used to detect an explosive target gas. Such a gas detection device typically comprises a radiation source, which emits electromagnetic radiation into an area to be monitored, as well as at least one photosensor, on which a portion of the emitted radiation impinges (is incident on), after the radiation has penetrated the area. The photosensor generates a signal as a function of the intensity of impinging electromagnetic radiation. An analysis unit analyzes the respective signal from the photosensor or from each photosensor of the gas detection device and generates a detection result, for example, an alarm, if the target gas is present, or an estimation of the concentration of the target gas. The gas detection device according to the present invention also operates in this manner.

Many gas detection devices known from the state of the art utilize the following principle: A target gas in the area to be monitored, which target gas shall be detected, attenuates the emitted electromagnetic radiation or absorbs it even completely in at least one wavelength range that is known and predefined beforehand. This attenuation or complete absorption leads to a changed signal of the photosensor or of a photosensor—compared with a state without the target gas to be detected. The analysis unit automatically detects these changes in the signal. The gas detection device according to the present invention likewise operates according to this principle.

It is possible that the gas detection device according to the present invention monitors a room in a building. In one possible application of the gas detection device according to the present invention, the area to be monitored is, by contrast, not arranged in the interior of a building. The area often does not even have a roof over it, but is located outdoors and is hence exposed to different, varying ambient conditions, especially rain, snow, fog, smoke and dust (open path application). Not only the target gas to be detected, but also water drops and other particles in the air may attenuate electromagnetic radiation. It is desired to distinguish the attenuation because of water from the attenuation because of a target gas to be detected in order to reliably detect the target gas and, moreover, in order to prevent a high number of false (false positive) alarms.

Different gas detection devices, which emit electromagnetic radiation and analyze signals, which have been generated by photodetectors, have become known.

WO 2014/113287 A1 shows a gas detection device (open path gas detection system), which is capable of detecting a target gas in an area (area 109). A radiation source (transmitter unit 105 with radiation source 114) emits a radiation into the area 109. An optical interference filter, for example, a wavelength-division multiplexing filter or a beam splitter, splits the impinging radiation into two wavelength ranges. A plurality of such optical components may be arranged in a cascaded manner. Radiation in the first wavelength range is reflected, and radiation in the second wavelength range is transmitted. Two detectors 128a, 128b as well as optionally additional photodiodes are capable of generating a respective signal as a function of the intensity of impinging radiation.

The gas detector system of DE 10 2012 007 561 A1 comprises a transmitter 1 with a light source 3, a reference filter 49', an analysis filter 43', a receiver detector 65, a reference detector 45 and an analysis detector 39, cf. FIG. 5. The reference filter 49' lets the wavelength range, in which a target gas absorbs electromagnetic radiation, as well as a range with shorter wavelengths, pass through and reflects the remaining part of the light. The light reflected by the reference filter 49' impinges on the receiver detector 65. The transmitted light impinges on the reference detector 45.

The gas detection device (non-dispersive infrared spectrophotometer) from US 2003/0 205 673 A1 comprises a radiation source (source 11 for infrared energy), three photodetectors 55, 57 and 59, a plurality of filters (dichroic mirrors 31, 33, narrow bandpass filters 43, 45, 47) and an analysis unit (signal processor). The bandpass filter 43 in front of the photodetector 55 lets wavelengths in a first range (carbon dioxide pass band 43f) pass through, the bandpass filter 45 in front of the photodetector 57 lets wavelengths in a second range (nitrous oxide pass band 45f) pass through, and the bandpass filter 47 in front of the photodetector 59 lets wavelengths in a reference range (reference pass band 47f) pass through.

The gas detection device from DE 10 2016 108 544 A1 comprises an IR radiation source S, which emits a bundle of rays with a continuous spectrum, five detectors D1 through D5 as well as a reference detector 9 and five bandpass interference filters F1 through F5. A gas to be monitored enters through a gas inlet 4 into a measurement area, which is penetrated by the IR radiation in a zigzag manner, and leaves the area through a gas outlet 5.

The device from DE 20 2011 102 765 U1 comprises a radiation source 4, which radiates light in an infrared wavelength range, a measuring detector 21, two reference detectors 25 and 27, a measuring wavelength filter element 22 in front of the measuring detector 21, two reference wavelength filter elements 26 and 28 in front of the reference detectors 25 and 27, respectively, an analysis device 8, an alarm generation device 18 and a display device 15.

SUMMARY

A basic object of the present invention is to provide a gas detection device for detecting a target gas in an area to be monitored as well as a process for monitoring an area for a target gas, wherein the gas detection device as well as the process are capable of detecting a certain predefined target gas more reliably than prior-art gas detection devices.

The object is accomplished by a gas detection device having detection device features according to the invention and a process having process features according to the invention. Advantageous embodiments are described. Advantageous embodiments of the gas detection device according to the present invention are, if meaningful, also advantages of the process according to the present invention and vice versa.

The gas detection device according to the present invention comprises
- a radiation source,
- a first gas photosensor,
- a second gas photosensor,
- a reference photosensor,
- an array of filters and
- a signal-processing analysis unit, preferably comprising one or more processors and a memory.

A first wavelength range, a second wavelength range and a reference wavelength range are predefined. A distance occurs between the first wavelength range and the second wavelength range. A respective distance likewise occurs between the reference wavelength range and the first wavelength range as well as between the reference wavelength range and the second reference wavelength range. The wavelength ranges thus do no overlap. The wavelength ranges are predefined as follows as a function of the target gas to be detected: The target gas to be detected attenuates electromagnetic radiation more intensely both in the first wavelength range and in the second wavelength range than radiation in the reference wavelength range, especially at least when the concentration of the target gas is above a detection limit.

The radiation source is capable of emitting electromagnetic radiation, for example, light in the visible range or ultraviolet radiation or infrared radiation. The wavelengths of the emitted radiation cover all three wavelength ranges. The radiation source is capable of emitting the electromagnetic radiation permanently in one embodiment and in a pulsed manner in another embodiment. The pulse rate may be constant over time or variable over time.

Each photosensor is capable of generating a respective signal, preferably an electrical signal, wherein the respective generated signal depends on the intensity of electromagnetic radiation, which impinges on (is incident on) the photosensor. As a rule, the value of the signal is greater, the greater is the intensity of the currently impinging radiation.

The analysis unit is in a respective data connection with the three photosensors and is capable of receiving and automatically analyzing the three signals from the three photosensors. Signals can be transmitted to the analysis unit via these data connections in a cabled and/or wireless manner, and especially by radio waves. The two signals from two different photodetectors may be transmitted to the analysis unit via the same data connection.

The gas detection device according to the present invention is configured to operate as follows, and the process according to the present invention comprises the following steps:

The radiation source emits electromagnetic radiation into a spatial area which is to be monitored for the presence of the gas ("target gas") which is predefined and is to be detected. This area may especially be a room in a building, vehicle or else, an area outside of a building.

At least a part of the emitted radiation penetrates the area at least once. It is possible that the radiation is reflected at least once and therefore penetrates the area multiple times, as a result of which the optical path is lengthened.

If the target gas to be detected is present in the area, then it attenuates the electromagnetic radiation emitted in the first wavelength range and/or in the second wavelength range, wherein the intensity of the attenuation varies, as a rule, with the wavelength of the emitted radiation, optionally additionally because of ambient conditions. As a result, the attenuation depends on the concentration of the target gas.

At least when no gas, which attenuates electromagnetic radiation, is present in the area to be monitored, at least a portion of the emitted electromagnetic radiation penetrates the area to be monitored and impinges on the array of filters.

The array of filters distributes impinging electromagnetic radiation onto the three photosensors, wherein the distribution of the radiation depends on the wavelength. As a result, only respective radiation in a certain wavelength range impinges on each photosensor. More precisely: Outside of this wavelength range, the intensity of the radiation impinging on the photosensor is below a predefined intensity limit, especially both when the target gas to be detected is present in the area and when it is not present. This wavelength range differs from photosensor to photosensor.

Each photosensor generates a respective signal as a function of the intensity of the impinging radiation.

The analysis unit receives these three signals and automatically analyzes them.

The array of filters distributes the electromagnetic radiation onto the photosensors such that at least when no gas, which is capable of attenuating electromagnetic radiation, is present in the area to be monitored, the following result is achieved:

A first portion of the impinging radiation, which portion is present in the first wavelength range, impinges on the first gas photosensor with an intensity above a predefined intensity limit, while radiation outside of the first wavelength range does not impinge on the first gas photosensor or only with an intensity below this intensity limit.

A second portion of the impinging radiation, which portion is present in the second wavelength range, impinges on the second gas photosensor with an intensity above a predefined intensity limit, while radiation outside of the second wavelength range does not impinge on the second gas photosensor or only with an intensity below this intensity limit.

A reference portion of the impinging radiation, which portion is present in the reference wavelength range, impinges on the reference photosensor with an intensity above a predefined intensity limit, while radiation in the first wavelength range and radiation in the second wavelength range do not impinge on the reference photosensor or only with an intensity below this intensity limit.

When the target gas to be detected is present, the radiation in the first wavelength range and/or in the second wavelength range may, by contrast, be attenuated up to below the intensity limit. Also, a different gas or water droplets or particles in the area to be monitored may attenuate radiation in the first wavelength range and/or in the second wavelength range.

The analysis unit receives the signals from the three photosensors and compares the received signals of the three photosensors with one another automatically. In one alternative, depending on the result of this comparison, the analysis unit automatically determines whether or not the target gas is present in the area to be monitored. In another alternative, the analysis unit determines, as a function of the comparison, an indicator of a concentration of the target gas in the area to be monitored—at least an approximation of the concentration of the target gas in the area to be monitored. The two alternatives can be combined with one another.

If the analysis unit has determined that the target gas to be detected is present, then the analysis unit preferably triggers an alarm on an alarm unit at a distance in space and/or outputs a message in a form perceptible by a person, for example, visually, acoustically or by touch (by vibrations being generated). In one embodiment, the gas detection device outputs the determined concentration of the target gas in a form perceptible by a person, for example, on a display unit of the gas detection device itself or on a display unit spaced at a distance from the detection device.

The present invention utilizes a principle, which is already known from the state of the art, namely the following: A radiation source radiates electromagnetic radiation into an area to be monitored. At least a portion of the radiation penetrates the area and impinges on a gas photosensor, which is especially sensitive in a certain wavelength range. A target gas to be detected absorbs a portion of the electromagnetic radiation in this wavelength range, and the gas photosensor detects this attenuation. In addition, the radiation impinges on a reference photosensor, which is especially sensitive in another wavelength range. If the target gas is present, then the gas photosensor detects a more intense attenuation than the reference photosensor; otherwise, the two photosensors send similar signals. In many cases, variable ambient conditions have an approximately similar effect on the signal from the gas photosensor and on the signal from the reference photosensor, so that the influence of the ambient conditions can be compensated by calculation up to a certain extent by means of the signal from the reference photosensor.

The principle of measuring the attenuation of electromagnetic radiation by the target gas avoids the need to use a chemical, which changes under the influence of a target gas to be detected, wherein the chemical change indicates (signalizes) the presence of the target gas to be detected and can be measured. Such a chemical must always be present in sufficient quantity during the use and must, of course, not be harmful to a person.

On the one hand, it is desired that a gas detection device be capable with high certainty of actually automatically detecting the target gas to be detected. This target gas is, for example, combustible or poisonous or harmful to humans for another reason, and a release of this target gas into the area to be monitored shall or must in many cases be detected rapidly and with certainty. On the other hand, it is desired that only relatively few false alarms occur. The event that the gas detection device reports the presence of the target gas to be detected, even though this target gas is not present or is at least not present with a relevant concentration in the area, shall thus occur only relatively rarely.

In many applications, the area to be monitored is exposed to environmental influences, for example, to the weather or other particles in the air, especially when the area is arranged outdoors. Especially when the area is exposed to environmental influences, liquid droplets and dust particles and other substances, which likewise absorb electromagnetic radiation, may reach the area to be monitored. These absorbing, but usually harmless substances do not need to be detected and shall, as a rule, not trigger an alarm. However, since they may distort the detection results, they are collectively called "contamination" below. An attenuation of the electromagnetic radiation may thus be caused by the target gas to be detected or else, exclusively by a contamination, which is not harmful and hence shall not trigger an alarm, or by a combination of both. In addition, it is possible that the intensity of the electromagnetic radiation which the radiation source emits or the sensitivity of a photosensor changes, especially decreases, in the course of time. The varying intensity of the radiation source is caused, for example, by an aging or other wear and tear of the radiation source itself or of a power supply unit of the gas detection device or by a contamination of the radiation source.

The just described contamination and the wear and tear have an approximately similar effect on the three signals of the three photosensors in many cases. The signal from the reference photosensor can be used in order to be able to distinguish the presence of a contamination and the effect of wear and tear from the presence of the target gas. The signal from the reference photosensor can also be used in many cases to compensate by calculation the influence of ambient conditions and of wear and tear on the two signals from the two gas photosensors up to a certain extent.

In a preferred embodiment, at least one reference comparison result is predefined in a form which can be analyzed by a computer. This reference comparison result describes a result, which is to be expected, if no gas that attenuates electromagnetic radiation is present in the area to be monitored, wherein the analysis unit in this case is capable of automatically detecting the reference comparison result. The analysis unit automatically determines whether or not the target gas to be detected is present in the area to be monitored as a function of the result, which the comparison of the three signals from the three photosensors has provided, and as a function of the preferred reference comparison result or of at least one predefined reference comparison result. The analysis unit determines, at least when the target gas is present, when the comparison yields the following result: The signal from the first gas photosensor and/or the signal from the second gas photosensor is attenuated more intensely in relation to the signal from the reference photosensor than in case of the reference comparison result. In other words: The target gas is detected when the signal strength from the first gas photosensor signal and/or from the second gas photosensor signal is lower in relation to the signal strength from the reference photosensor signal, i.e., the signal is attenuated more intensely than this is the case according to the reference comparison result in case of a state free from the target gas and thus in case of the reference comparison result. It is possible that only the signal from one gas photosensor is attenuated by the target gas. It is also possible that the signals from both gas photosensors are attenuated.

According to this embodiment, a reference comparison result is thus predefined. This reference comparison result describes what result a comparison of the three signals of the three photosensors has, if the target gas is not present in the area. A possible embodiment is that all three photosensors send the same signal in the absence of target gas. However, it is also possible that the three photosensors all use at least two different measurement principles and therefore also when no gas, which attenuates radiation, is present, at least two signals are distinguished from one another, and especially because of the construction of the gas detection device. The reference comparison result describes this difference in case of a state free from the target gas.

The device according to the present invention and the process according to the present invention are capable in many cases of detecting the presence of the target gas to be detected with greater certainty with fewer false alarms than prior-art devices and processes. One reason for this is explained below.

The device makes use of the fact that many gases to be detected, especially hydrocarbons such as methane, propane and ethylene, attenuate electromagnetic radiation in at least two different wavelength ranges, wherein a distance occurs between these two wavelength ranges, i.e., an intermediate wavelength range, in which target gas practically does not attenuate electromagnetic radiation or in any case attenuates electromagnetic radiation markedly less. These two absorbing wavelength ranges are used as the first wavelength range and the second wavelength range of the present invention. "Attenuation" means an absorption of the radiation with a degree of absorption above a predefined detection limit. According to the present invention, a distance occurs (no overlap) between these two wavelength ranges, i.e., the intermediate wavelength range. The target gas to be detected attenuates the radiation less intensely in this intermediate wavelength range than in the first wavelength range and in the second wavelength range. The reference wavelength range may be in this intermediate wavelength range.

As a rule, it is predefined, for which target gas the area shall be monitored, and it is known how intensely the target gas attenuates electromagnetic radiation for the concentrations being considered during the operation. This attenuation depends, as a rule, on the wavelength λ of the emitted electromagnetic radiation. As a rule, it is thus known how high the absorption rate and thus the degree of transmission of this target gas are as a function of the wavelength λ of the radiation. The two absorbing wavelength ranges are, as a rule, likewise known by the target gas being predefined and its absorption characteristic being known.

The array of filters determines the wavelength ranges, in which the photosensors are sensitive. It is possible, but not necessary in many cases, to adapt the photosensors to the target gas. It is sufficient to adapt the array of filters.

The gas detection device according to the present invention, especially the array of filters, can be configured and calibrated, after predefining a target gas to be detected, such that this target gas to be detected attenuates electromagnetic radiation both in the first wavelength range and in the second wavelength range of the array of filters above the detection limit but not in the reference wavelength range. As a rule, it is known how intensely the target gas absorbs electromagnetic radiation in the first wavelength range and how intensely target gas absorbs and as a result absorbs electromagnetic radiation in the second wavelength range and how sensitive the two respective gas photosensors are to impinging radiation. The attenuation depends, as a rule, on the concentration of the target gas and may also depend on environmental influences. The two wavelength ranges can, by contrast, in many cases be set such that the target gas in any concentration occurring in practice attenuates the radiation in a detectable manner only in these wavelength ranges.

It is possible that not only the target gas, but also a contamination of the area to be monitored or an aging or contamination of the radiation source leads to radiation being significantly attenuated in the first wavelength range or radiation being significantly attenuated in the second wavelength range. As a rule, the radiation is, however, not attenuated significantly in both wavelength ranges. A gas detection device with a single gas photosensor for this target gas, which is inevitably sensitive only in a single wavelength range, could not in this case distinguish an attenuation of the signal because of a contamination or aging in many cases from an attenuation because of the target gas to be detected with enough certainty. Precisely in this situation, the gas detection device according to the present invention yields a higher reliability, because, as a rule, a contamination in the area to be monitored or an aging of the radiation source does not generate an intense attenuation similar to the target gas to be detected both in the first wavelength range and in the second wavelength range and, moreover, no relevant attenuation even in the reference wavelength range. The distances between the wavelength ranges contribute to this higher reliability.

Gas detection devices have become known, which comprise at least two different photosensors for different wavelength ranges, wherein each photosensor is assigned to a respective target gas to be detected and is especially sensitive in the wavelength range, in which this target gas intensely attenuates electromagnetic radiation. Such a gas detection device is thus capable of detecting at least two different target gases. Also in this prior-art embodiment, by contrast, only one respective photosensor and optionally a reference photosensor are present for each target gas, but not two different photosensors for the same target gas as in the gas detection device according to the present invention. In such a prior-art gas detection device, a contamination may thus lead more frequently to a false alarm or else, to a target gas not being detected.

The gas detection device according to the present invention offers an increased reliability and, in addition, redundancy: It is capable of detecting the target gas in many cases even if one of the two photosensors is contaminated or defective or not connected to the analysis unit or if, even though all the photosensors are intact, the target gas to be detected significantly attenuates electromagnetic radiation only in one of the two wavelength ranges because of a special ambient condition.

According to the present invention, the signals of the first gas photosensor are only influenced by an attenuation of the electromagnetic radiation in the first wavelength range, the signals of the second gas photosensor only by an attenuation in the second wavelength range and the signals of the reference photosensor only by an attenuation in the reference wavelength range. This is essentially brought about by the array of filters. It is possible, but not necessary thanks to the array of filters according to the present invention to use different photosensors, and especially photosensors with different sensitivities to the three wavelength ranges. The sensitivity of a photosensor may change over the course of time, so that a gas detection device, which depends highly on the sensitivities of the photosensors, ages relatively rapidly and/or has to be readjusted relatively frequently. By contrast, the gas detection according to the present invention changes its sensory properties only relatively slowly. As a result, a readjustment is rarely necessary.

In case of many prior-art gas detection devices, signals are available to the analysis unit from only two photosensors, namely from a gas photosensor, which reacts to the attenuation of radiation by a target gas to be detected, as well as from a reference photosensor, which is not at all sensitive or less sensitive to this attenuation and environmental influences can be compensated by calculation with the signal thereof. By contrast, according to the present invention, signals from three photosensors, including signals from two gas photosensors, which are capable of detecting an attenuation in two different wavelength ranges, are simultaneously available to the analysis unit, wherein a distance occurs (there is no overlap) between these two wavelength ranges and wherein, as a rule, the target gas brings about a respective attenuation in both wavelength ranges. As a result, the gas detection device according to the present invention generates in many cases fewer false alarms, compared with prior-art devices, especially in case of a contamination of the area to be monitored.

Moreover, the gas detection device according to the present invention is less sensitive to a gradual change in the intensity or in another property of the electromagnetic radiation, which the radiation source emits, i.e., it is less sensitive to aging. Such a gradual change may occur, for example, due to an aging or contamination of the radiation source or due to a change in a power supply unit for the radiation source. This gradual change has, as a rule, a relatively similar effect on the intensities that the three photosensors detect and can therefore be compensated by calculation up to a certain extent—more precisely: A target gas is detected with sufficiently high reliability and is distinguished from a contamination despite the gradual change. It is not necessary to quantitatively measure a gradual change of the radiation source. The gas detection device according to the present invention is also less sensitive to a gradual change of a photosensor, e.g., because of aging or gradual contamination.

It is possible that a gas photosensor fails or that because of a blocking or a contamination, no more radiation at all impinges on a gas photosensor. The gas detection device according to the present invention is capable of automatically detecting this situation in many cases, especially because the two signals from the two gas photosensors can be compared. In addition, the gas detection device is frequently capable of still detecting the target gas even in case of the failure of a photosensor, even though in many cases with a lower reliability and/or with more false alarms.

According to the present invention, the gas detection device comprises a first gas photosensor, on which radiation impinges in the first wavelength range, and a second gas photosensor, on which radiation impinges in the second wavelength range. The present invention makes it possible to use two different photosensors as the two gas photosensors, wherein the two photosensors are adapted to these two wavelength ranges and have a sufficiently high sensitivity with good reliability. It is also possible to use two photosensors similar to the two gas photosensors. The reference photosensor may be configured just like at least one gas photosensor or may be distinguished from the two gas photosensors.

According to the present invention, the analysis unit automatically analyzes the three signals from the three photosensors in order to determine whether or not the target gas is present, or to determine the target gas concentration. When analyzing the signals from the three photosensors, the analysis unit preferably automatically carries out the following steps:

The analysis unit carries out a respective pair comparison for each pair of two photosensors, i.e., a total of three pair comparisons, namely a pair comparison for the first gas photosensor and for the second gas photosensor, a pair comparison for the first gas photosensor and for the reference photosensor and a pair comparison for the second gas photosensor and for the reference photosensor.

The analysis unit compares the two signals from the two photosensors of the pair comparison with one another during each pair comparison.

The analysis unit determines as a function of the result of these three pair comparisons whether or not the target gas to be detected is present in the area to be monitored.

The analysis unit is configured to carry out these steps automatically. For example, the analysis unit is programmed correspondingly.

In many prior-art devices and processes, the signals of a gas photosensor are compared with the signals of a reference photosensor. In this case, a single comparison is also carried out in order to determine whether or not a target gas is present in the area to be monitored. By contrast, according to the preferred embodiment of the present invention, three pair comparisons are carried out, namely preferably carried out at each scanning time, at which a result shall be available. This is possible because according to the present invention three photosensors are present for the same target gas and not only two. In each pair comparison signals from two respective photosensors are compared with one another, namely the signals from the first gas photosensor and from the second gas photosensor, the signals from the first gas photosensor and from the reference photosensor, as well as the signals from the second gas photosensor and from the reference photosensor.

If the target gas to be detected is present in the area, then, as a rule, both the signal from the first gas photosensor and the signal from the second gas photosensor are attenuated. In the ideal case, the signal of the reference photosensor is not attenuated at all. In practice, the reference signal is often likewise attenuated because of contamination, but less intensely than the signals of the two gas photosensors or at least less intensely than the signal of one gas photosensor. Due to the three pair comparisons, this significant attenuation of the signals of at least one gas photosensor can be detected and be automatically distinguished from an attenuation only because of a contamination. In addition, it can be detected, when only one gas photosensor signal is attenuated significantly, which is often an indicator of a contamination or a failure or blocking. The distinction between an attenuation because of the target gas to be detected and an attenuation because of a contamination is improved by a respective distance occurring between the wavelength ranges and the target gas to be detected generating the attenuation just in the first wavelength range and in the second wavelength range, but not at all or at least less intensely in the reference wavelength range.

If the target gas to be detected is not present, then the signals from the two gas photosensors are, as a rule, not significantly more intensely attenuated than the signals of the reference photosensor. Ideally, i.e., if neither the target gas nor a contamination nor a wear and tear or aging is present, the pair comparison always yields the same result for the two gas photosensors, which depends only on the configuration of the gas detection device. In many cases, the concentration of the target gas has an only relatively minimal effect on the pair comparison for the two gas photosensors. In practice, a contamination brings about either a lower attenuation in the first wavelength range and/or in the second wavelength range compared with the target gas to be detected. Or else, the contamination attenuates radiation in all three wavelength ranges and thus signals of all three photosensors, but the attenuation is in each case to a different extent.

In one embodiment, at least one desired result is predefined for the pair comparison between the two signals of the two gas photosensors. This desired result is achieved, for example, when the area to be monitored is free from a contamination and free from the target gas to be detected or even is free from a contamination, but contains the target gas in a certain concentration. The actual result of this desired result of the pair comparison depends, though, on the concentration of the target gas to be detected. An actual result, which deviates sharply from the desired result, is caused, however, in many cases by a contamination of the area to be monitored, wherein this contamination has a markedly stronger or markedly weaker effect on the first wavelength range than on the second wavelength range. In other words: A possible contamination affects the result of the pair comparison between the two gas photosensor signals in many cases more strongly than the concentration of the target gas. The actual result of this pair comparison can be used for compensating by calculation up to a certain extent the effect of this contamination on the result of the remaining two pair comparisons and for distinguishing the presence of the target gas from this contamination with certainty despite a relevant contamination. Such a pair comparison and such a compensation by calculation would not be possible or it would be possible at least with less certainty in a gas detection device with only one gas photosensor.

The analysis unit especially preferably forms a respective quotient between two signal values from the two photosensors involved, preferably a quotient again at each scanning time, during each pair comparison. This configuration requires relatively little computing time—compared with other possible configurations of the pair comparisons.

The electromagnetic radiation, which the radiation source emits, covers all three wavelength ranges. The electromagnetic radiation is preferably emitted in a pulsed manner, especially in order to save energy. In one embodiment, the radiation of each pulse covers all three wavelength ranges. In another embodiment, radiation is emitted alternately in the pulses in the first wavelength range, in the second wavelength range and in the reference wavelength range. In this embodiment, the analysis unit uses the signals that have been generated in at least three pulses for the three wavelength ranges.

According to the present invention, the array of filters distributes the impinging electromagnetic radiation onto the three photosensors, namely as a function of the wavelengths. In one embodiment, the array of filters comprises a first optical filter and a second optical filter. Viewed in the radiation direction, the second optical filter is arranged downstream of the first optical filter. The first optical filter is therefore located between the area to be monitored and the second optical filter. The first optical filter is capable of reflecting electromagnetic radiation in the first wavelength range and of transmitting (of letting through) electromagnetic radiation outside of the first wavelength range. The radiation, which the first optical filter has reflected, impinges on the first gas photosensor. The radiation, which the first optical filter has transmitted, impinges on the second optical filter.

The second optical filter transmits impinging electromagnetic radiation in the second wavelength range in a first alternative of this embodiment. This transmitted radiation impinges on the second gas photosensor. The second gas photosensor is thus arranged downstream of the second optical filter. The second optical filter reflects impinging electromagnetic radiation outside of the second wavelength range. This reflected radiation impinges completely or at least partially on the reference photosensor. Radiation outside of the first wavelength range and outside of the second wavelength range is thus transmitted by the first optical filter and reflected by the second optical filter.

The second optical filter reflects impinging electromagnetic radiation in the second wavelength range in a second alternative of this embodiment. This reflected radiation impinges on the second gas photosensor. The second optical filter transmits impinging electromagnetic radiation outside of the second wavelength range. This transmitted radiation impinges on the reference photosensor completely or at least partially. The reference photosensor is thus arranged downstream of the second optical filter. Radiation outside of the first wavelength range and outside of the second wavelength range is thus transmitted by the two optical filters.

Note: As a rule, of course, radiation losses occur during reflection and transmission. The terms "transmit" and "reflect" do not necessarily mean a 100% transmission or a 100% reflection. Rather, they mean that a greater part of the radiation is reflected in the respective wavelength range than is transmitted or a greater portion is transmitted than is reflected.

The just described embodiment, in which a second optical filter is arranged downstream of the first optical filter and both optical filters transmit or reflect as a function of the wavelength, makes possible in many cases an especially compact configuration of the gas detection device according to the present invention. This advantage is achieved especially because the size of the gas detection device at right angles to the direction, in which electromagnetic radiation impinges on the first optical filter, can be kept relatively small. In addition, it is sufficient when the electromagnetic radiation is focused sharply, i.e., it has a relevant intensity only within a relatively small area obliquely to the radiation direction. This embodiment saves energy that has to be generated for the radiation source.

In addition, according to this embodiment, electromagnetic radiation does not penetrate the array of filters in the first wavelength range, but is reflected. This leads in many cases to a lower loss of radiation energy and radiation intensity, compared with an embodiment, in which this radiation would have to penetrate at least one filter. Therefore, the just described embodiment is especially advantageous when the wavelengths of the first wavelength range are greater than the wavelengths of the other two wavelength ranges. In this case, the radiation in the first wavelength range has, as is known, a lower frequency than the radiation in the other wavelength ranges and therefore also a lower intensity.

In another embodiment, the three photosensors are arranged parallel to one another. The array of filters comprises a first detector filter, a second detector filter and a reference detector filter. The first detector filter is located between the area to be monitored and the first gas photosensor and lets only radiation in the first wavelength range pass through. The second detector filter is located between the area to be monitored and the second gas photosensor and lets only radiation in the second wavelength range pass through. The reference detector filter is located between the area to be monitored and the reference photosensor and lets only radiation outside of the first wavelength range and outside of the second wavelength range pass through, preferably only radiation in the reference wavelength range. The three detector filters are also arranged parallel to one another.

The emitted electromagnetic radiation needs only to pass through one wavelength filter, namely a detector filter, before it impinges on a photosensor in this embodiment. This applies to each wavelength of the radiation. This leads in some cases to a lower loss of radiation intensity and thus of radiation energy compared with other possible embodiments.

The present invention and the just described embodiments provide a reference wavelength range and a reference photosensor. It is possible that an additional reference wavelength range is predefined, which is spaced apart from (does not overlap with) the first wavelength rage, from the second wavelength range and from the reference wavelength range. The emitted radiation covers both reference wavelength ranges. Optionally, the gas detection device comprises an additional reference photosensor, overall also at least two reference photosensors. The array of filters splits up impinging electromagnetic radiation according to the present invention and, in addition, such that radiation in the additional reference wavelength range impinges on the additional reference photosensor. This embodiment increases the reliability and reduces the risk of false alarms further, because a contamination and often also a wear and tear have, as a rule, a different effect on the two reference wavelength ranges. In addition, this embodiment creates additional redundancy: A gas detection device, which has according to the present invention two gas photosensors and two reference photosensors, may also still detect the target gas when both a gas photosensor and a reference photosensor have failed.

In a variant of this embodiment, the array of filters comprises the two above-described optical filters and a third optical filter. Each of these three optical filters is capable of reflecting or transmitting impinging electromagnetic radiation as a function of the wavelength. Electromagnetic radiation in one of the two reference wavelength ranges as well as in the second wavelength range passes through the first optical filter and impinges on the second optical filter. The second optical filter splits up this radiation such that radiation in the second wavelength range impinges on the second gas photosensor and radiation outside of the wavelength range, but at least radiation in the reference wavelength range, impinges on the third optical filter. The third optical filter splits up impinging radiation such that radiation in the reference wavelength range impinges on the reference photosensor and radiation in the additional reference wavelength range impinges on the additional reference photosensor. In some cases, this embodiment further increases the reliability of the gas detection device. The gas detection device with two reference photosensors is still less sensitive to different kinds of contaminations.

In a preferred embodiment, the first wavelength range consists of longer wavelengths than the second wavelength range. The first wavelength range especially preferably consists also of longer wavelengths than the reference wavelength range.

In one embodiment, the first gas photosensor comprises a type II semiconductor diode, especially an InAsSb photosensor. The reference photosensor and the second gas photosensor each comprise an InGaAs photosensor. A type II semiconductor diode is in many cases especially sensitive to longer wavelengths, and an InGaAs photosensor is in many cases especially sensitive to shorter wavelengths. This embodiment is preferably combined with the embodiment in which the first wavelength range consists of longer wavelengths than the two other wavelength ranges.

In one embodiment, the gas detection device comprises a separate power supply unit, for example, at least one rechargeable battery. As a result, the gas detection device can be operated independently of a stationary power supply network. It is made possible to set up at least one gas detection device according to the present invention, preferably a plurality of gas detection devices according to the present invention, at different positions of a larger area to be monitored, for example, of a refinery or other production plant. Each gas detection device is capable of generating an alarm and of transmitting the alarm by radio waves to a central receiver and/or of outputting the alarm in a form perceptible by a person.

It is also possible to configure the gas detection device as a portable device, which a user carries with him, while he stays in an area, in which the target gas to be detected may be present. If the portable gas detection device has detected the target gas, then it outputs an alarm in a form perceptible by a person, especially visually, acoustically or by touch (by the device vibrating).

In a preferred embodiment, the gas detection device comprises a transmitting unit and a receiving unit. The transmitting unit comprises the radiation source. The receiving unit comprises the photosensors, the array of filters and preferably also the analysis unit. The distance between the transmitting unit and the receiving unit can preferably be changed to adapt the gas detection device to spatial conditions of the area to be monitored. It is also possible that the analysis unit is arranged at a distance in space from the receiving unit and is in a data connection with the receiving unit.

The present invention pertains, furthermore, to such a receiving unit. This receiving unit comprises the three photosensors, the array of filters and preferably also the analysis unit.

In a variant of the embodiment with the transmitting unit and the receiving unit, the gas detection device comprises a transmitter-side housing and a receiver-side housing. The transmitting unit is accommodated in the transmitter-side housing. The photosensors and the array of filters are accommodated in the receiver-side housing. The analysis unit may likewise be accommodated in the receiver-side housing or at a spaced distance from the receiver-side-housing, for example, in a central computer. The two housings can be positioned such that the area to be monitored is located between the two housings and the emitted electromagnetic radiation passes through the area, before it reaches the receiver-side housing. The distance between the two housings can be changed. As a result, it is made easier in many cases to position the two housings.

The gas detection device according to the present invention can be used for detecting as target gas a gas, which attenuates electromagnetic radiation only in the first wavelength range and in the second wavelength range in a detectable manner, but not outside of these two wavelength ranges and especially not in the reference wavelength range.

In one embodiment, the gas detection device according to the present invention can be used for detecting at least two different target gases. The gas detection device comprises a selection unit, with which a user can predefine which target gas the gas detection device shall detect. Each detectable target gas attenuates the electromagnetic radiation in two respective wavelength ranges, which are spaced apart from one another. The analysis unit is adapted to the selection of a target gas and uses especially the assigned reference comparison result. The remaining components of the gas detection device preferably remain unchanged, i.e., they do not depend on the selection of the target gas.

The gas detection device according to the present invention can, for example, be used for detecting the release of a combustible target gas in a plant or in a vehicle, wherein this plant or this vehicle is exposed to environmental influences. It can also be used for detecting an anesthetic in the air in a room of a hospital.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
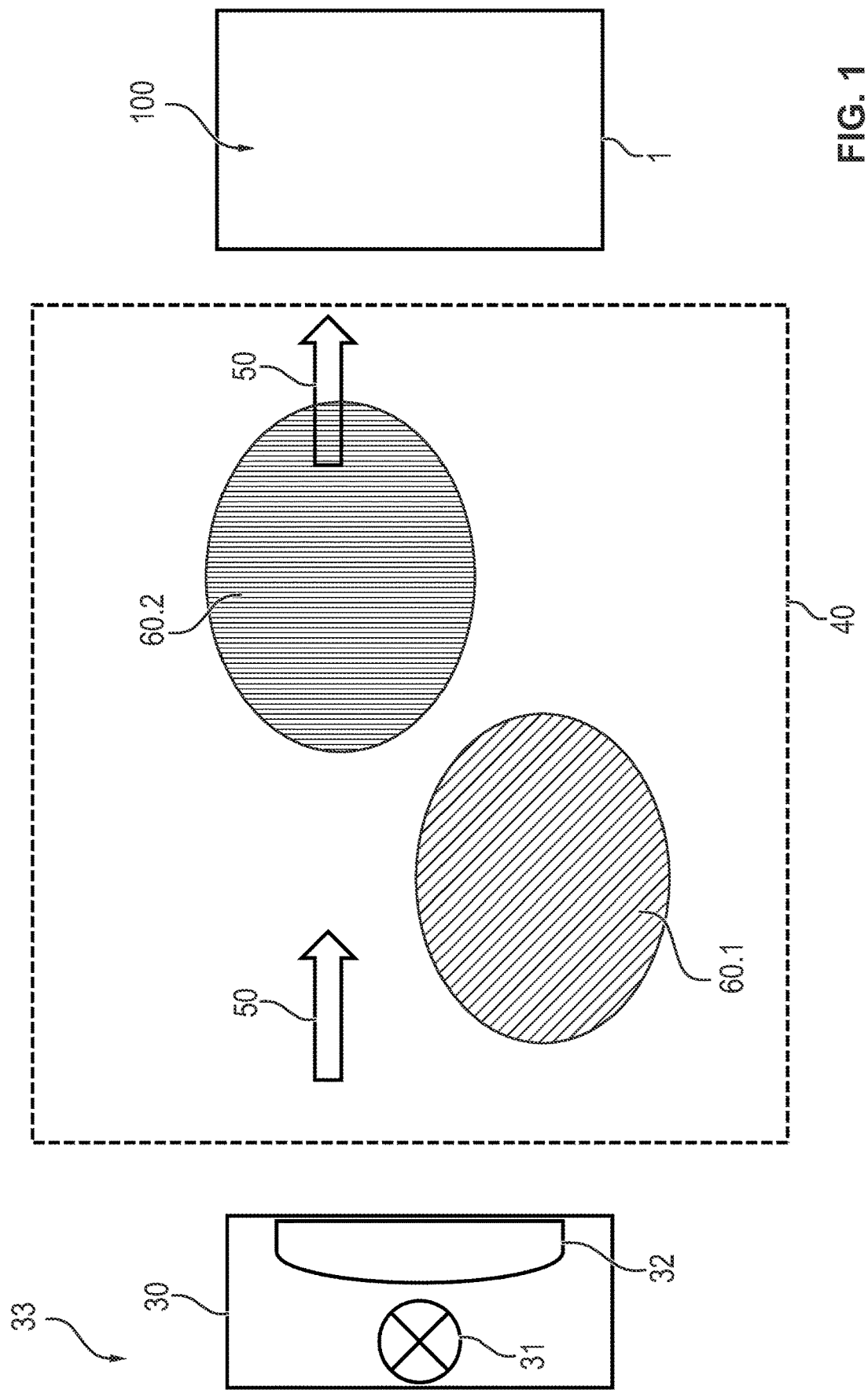
FIG. 1 is a schematic view showing the gas detection according to the present invention and the area to be monitored.

Referring to the drawings, FIG. 1 schematically shows a gas detection device as well as an area 40 to be monitored. The gas detection device according to the present invention of the exemplary embodiments are configured as shown in FIG. 1. For example, two gas clouds 60.1 and 60.2 containing a hazardous target gas are shown in the area 40 to be monitored, wherein the presence of this target gas shall be detected.

A transmitting unit 33 with a transmitter-side housing 30 and a receiving unit 100 with a receiver-side housing 1 belong to the gas detection device. The area to be monitored is located between these two housings 30 and 1 in the exemplary embodiment. The distance between these two housings 30 and 1 and thus the distance between the transmitting unit 33 and the receiving unit 100 can be changed to adapt the gas detection device to conditions in the area 40 to be monitored.

A radiation source 31 and a convergent lens 32 are accommodated in the transmitter-side housing 30; both likewise belong to the transmitting unit 33. The radiation source 31 emits electromagnetic radiation 50 into the area 40 to be monitored. This radiation source 31 preferably emits electromagnetic radiation with high radiation intensity in short pulses. The duration of a single such emitted radiation flash is, for example, between 20 µs and 100 µs. In the exemplary embodiment, the wavelength of the emitted electromagnetic radiation 50 varies over time, and especially at least between 2 µm and 4 µm. Therefore, the radiation 50 covers all three wavelength ranges described below. It is also possible that the radiation source 31 emits electromagnetic radiation 50, which covers the entire wavelength range from 2 µm to 4 µm, during each pulse.

At least a portion of the emitted electromagnetic radiation 50 penetrates the area 40 and impinges on (is incident on) the receiver-side housing 1. It is possible that a mirror (not shown) reflects the radiation 50 in order to lengthen the optical path.

A receiver unit 100, which will be described in more detail below, is arranged in the receiver-side housing 1. The target gas in the gas clouds 60.1 and 60.2 attenuates the emitted electromagnetic radiation 50 in certain wavelength ranges or absorbs this radiation 50 even completely.

Figure 2:
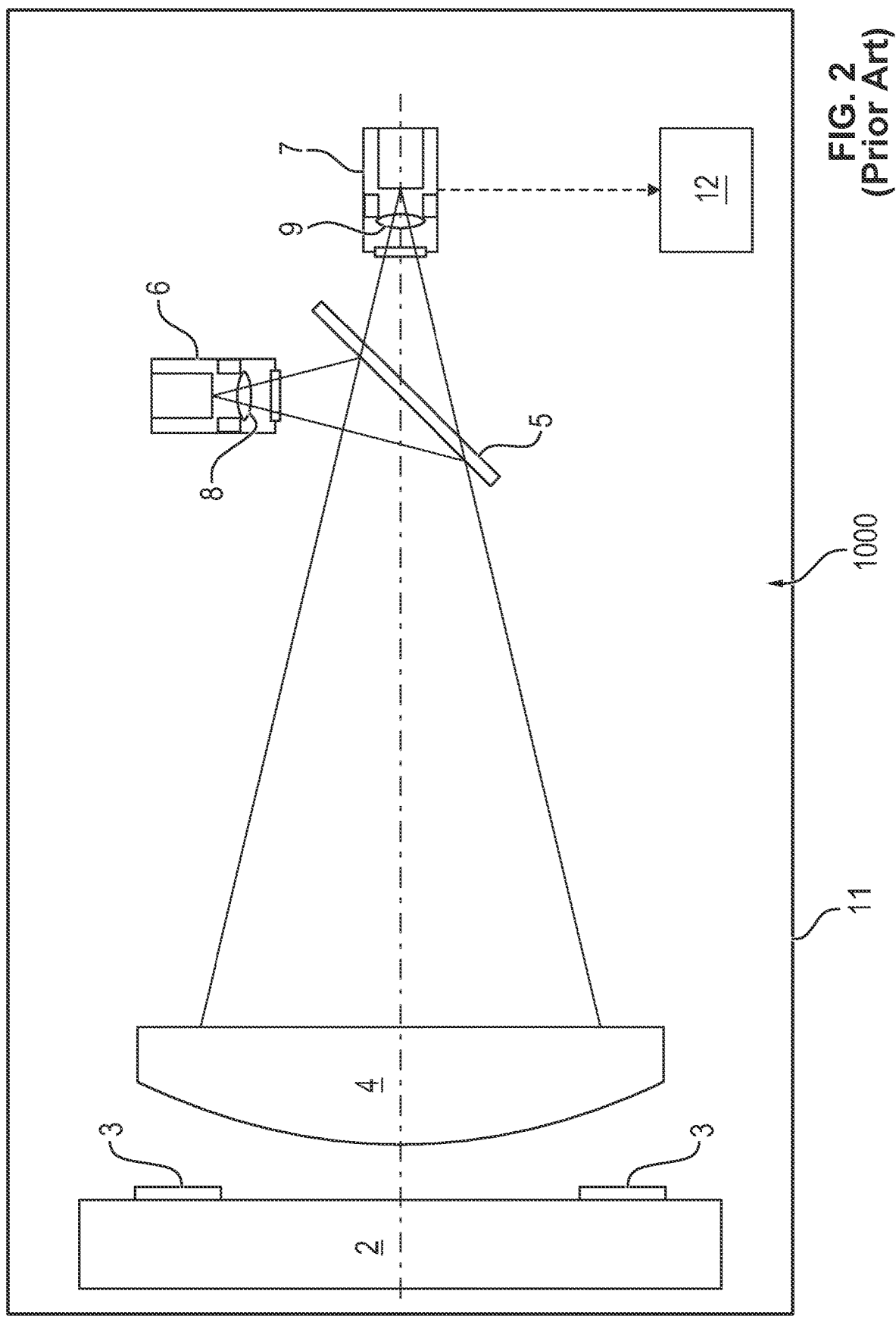
FIG. 2 is a schematic view showing a receiving unit of a gas detection device according to the prior art.

FIG. 2 shows an embodiment of a receiving unit 1000 in case of a gas detection device known from the state of the art. The emitted electromagnetic radiation penetrates the area to be monitored and then impinges on the receiving unit 1000, which is accommodated in the receiver-side housing 11. The impinging electromagnetic radiation penetrates an uncoated window 2 in the receiver-side housing 11, which is optionally heated by heating elements 3, to vaporize condensing or already condensed moisture. A convergent lens 4 with a convex surface pointing towards the window 2 and with a planar surface on the other side bundles the impinging electromagnetic waves. An optical filter 5 splits up the bundled waves. A first wave bundle is reflected, for example, by 90°, and impinges on a first detector 6. A second wave bundle penetrates (is transmitted through) the optical filter 5 and reaches a second detector 7. A first optical detector filter 8 of the first detector 6 as well as a second optical detector filter 9 of the second detector 7 filter out predefined wavelength ranges, for example, a wavelength range, in which radiation is attenuated by a target gas to be detected, and a wavelength range, in which the radiation is not attenuated by the target gas.

In the exemplary embodiment, the gas detection device according to the present invention is used for monitoring an area, which is not roofed over and is hence exposed to environmental effects, especially water molecules and dirt (open path application). The water molecules influence the so-called atmospheric window, which describes the transmission of light through the atmosphere. Water molecules absorb electromagnetic energy to a considerable extent and as a function of the wavelength of impinging electromagnetic radiation.

Figure 3:
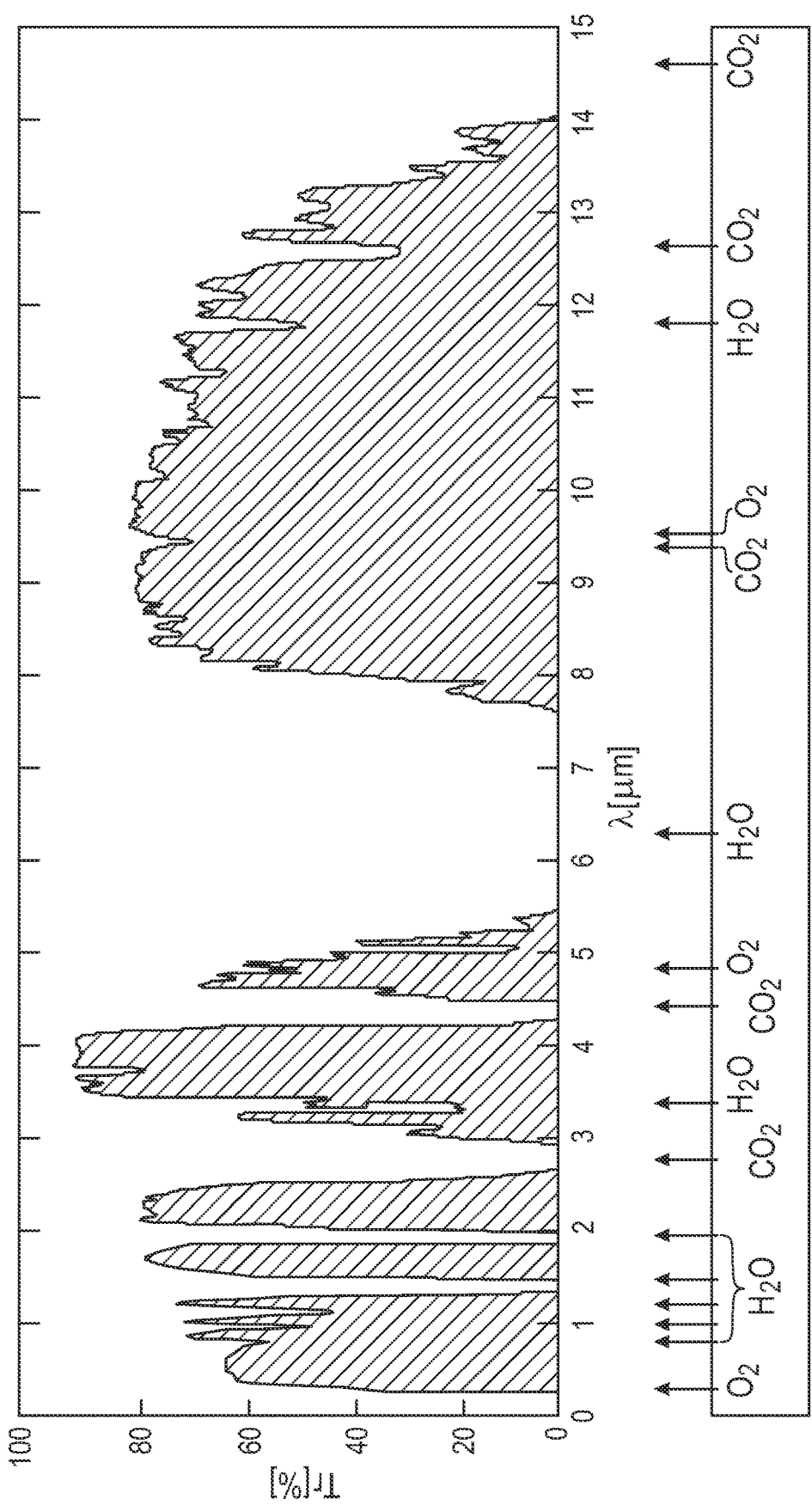
FIG. 3 is a graph showing the influence of water molecules on the degree of transmission as a function of the wavelength of the emitted radiation.

FIG. 3 shows an atmospheric window. The wavelength λ in micrometers is plotted on the x axis, the relative degree of transmission (relative permeability) Tr in % of electromagnetic radiation 50 as a function of the respective wavelength λ is plotted on the y axis. In addition, wavelength ranges are shown, in which the radiation is absorbed especially intensely by water molecules or ozone molecules. These molecules represent a contamination of the area 40 to be monitored, but are not hazardous and shall not trigger an alarm since such an alarm would be a false alarm.

Three possible hazardous target gases, which may be present in the form of gas clouds 60.1, 60.2 in the area 40 to be monitored and which shall be detected, are the hydrocarbons methane, propane and ethylene. FIG. 4 through FIG. 7 show, as an example, the respective spectral curve, i.e., the respective degree of transmission Tr in %, of these three hydrocarbons as a function of the wavelength λ of impinging electromagnetic radiation 50, wherein the radiation source 31 emits such radiation 50. The wavelength λ in micrometers [μm] between 2 μm and 4 μm is plotted on the x axis, and the degree of transmission Tr in % is plotted on the y axis. The lower the degree of transmission Tr is, the greater is the degree of absorption, i.e., the portion of absorbed radiation.

Figure 4:
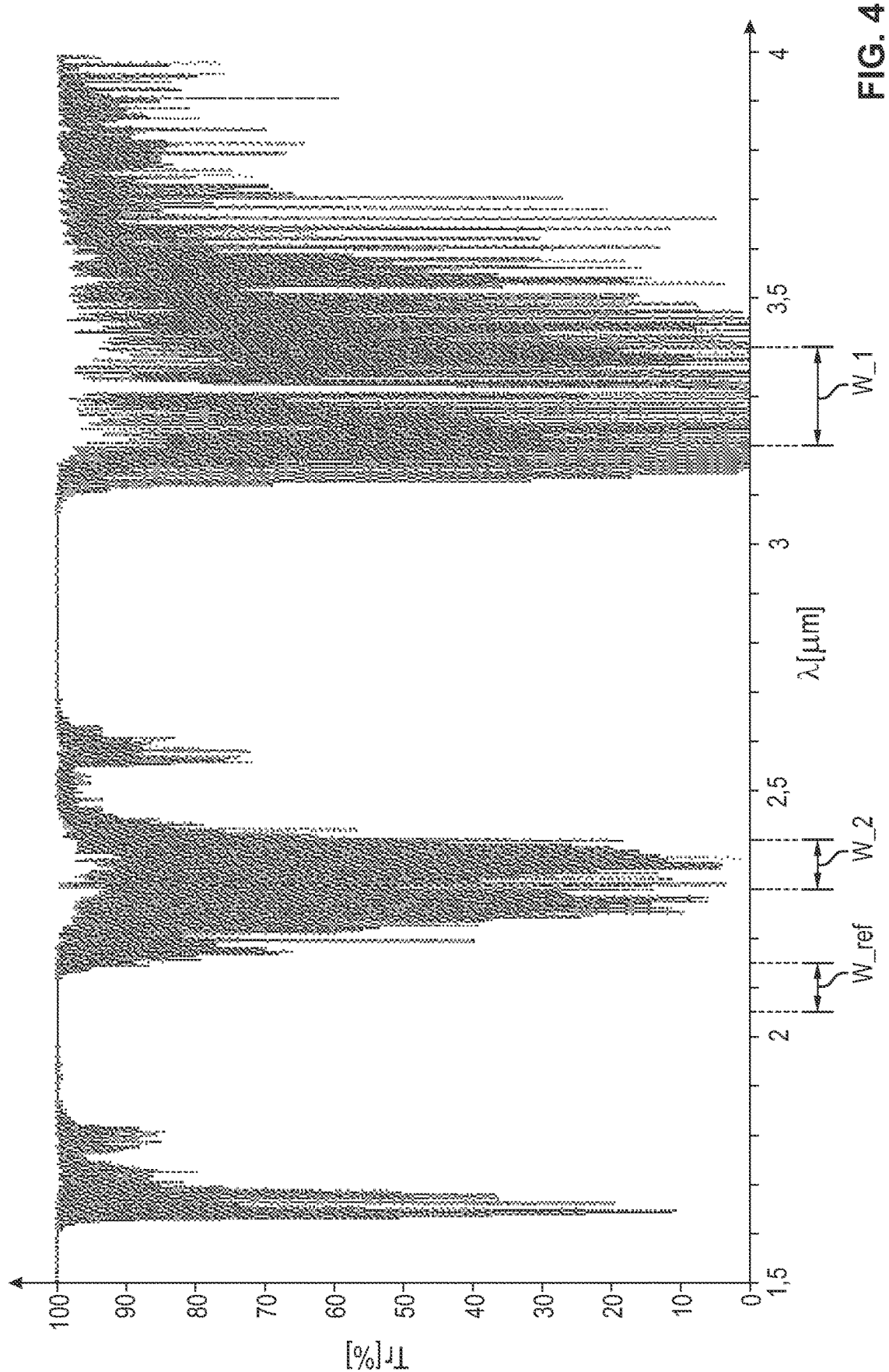
FIG. 4 is a graph showing the degree of transmission of methane of a relatively high concentration as a function of the wavelength.
Figure 5:
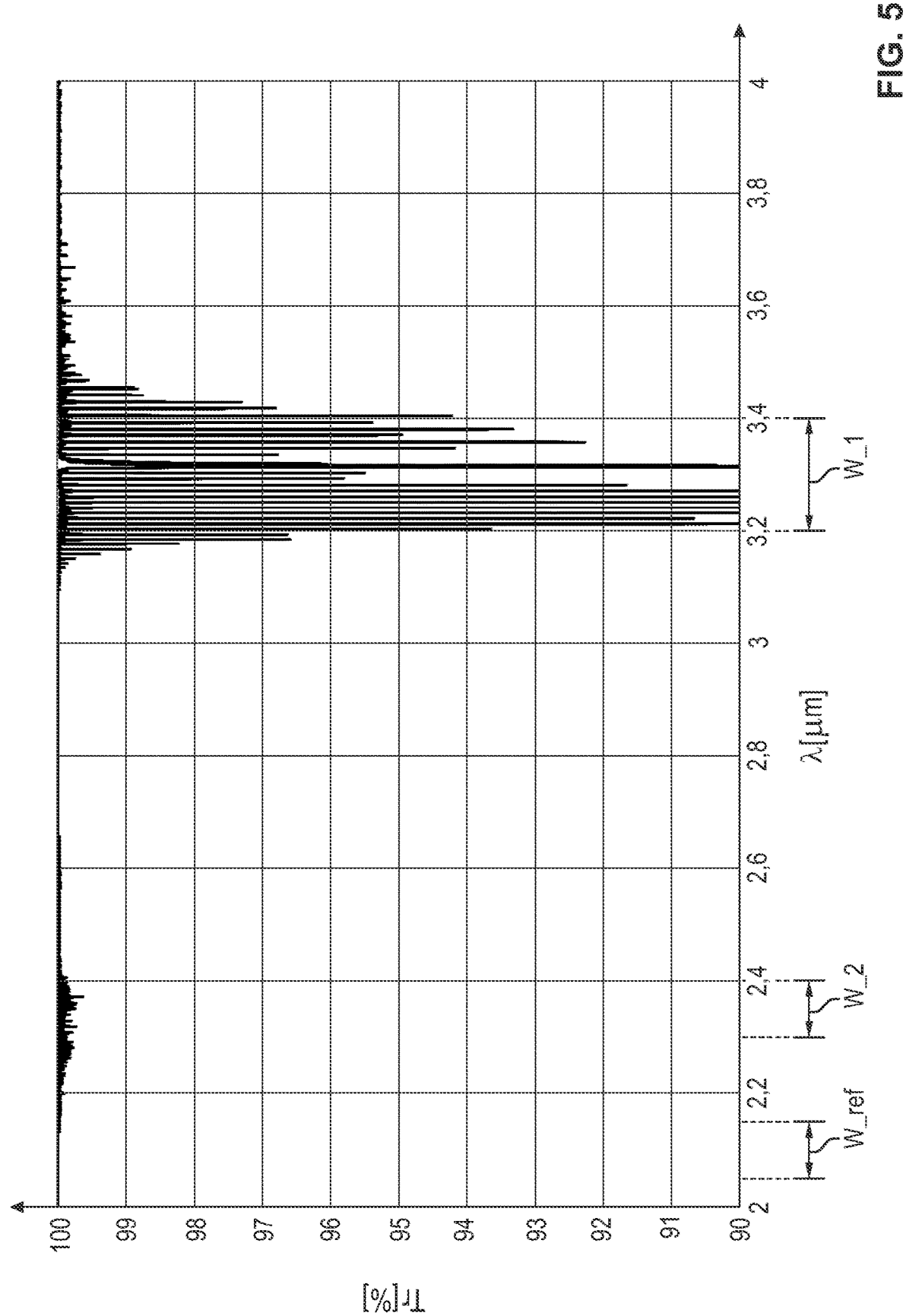
FIG. 5 is a graph showing the degree of transmission of methane of an average concentration as a function of the wavelength.
Figure 6:
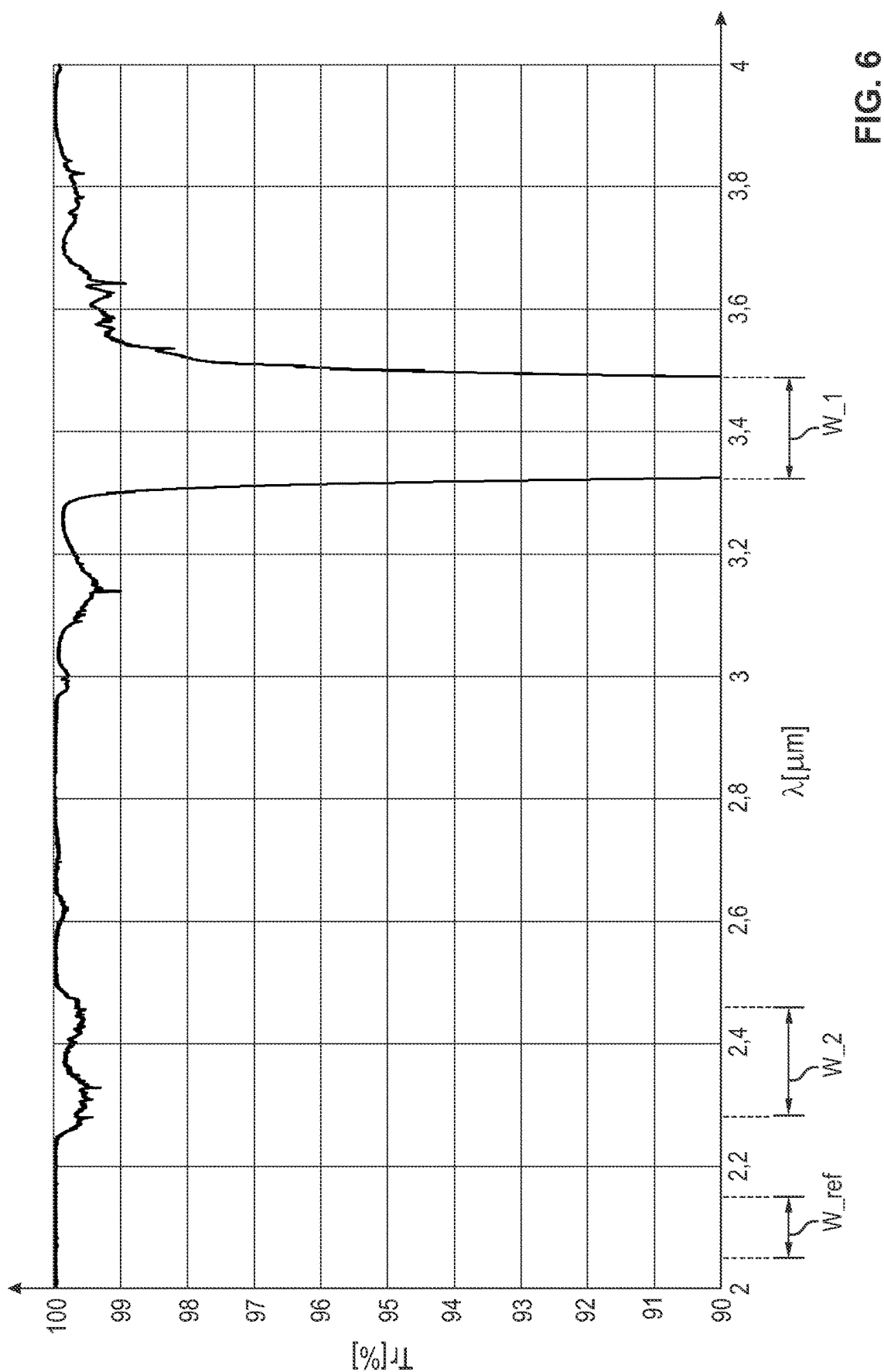
FIG. 6 is a graph showing the degree of transmission of propane of an average concentration as a function of the wavelength.
Figure 7:
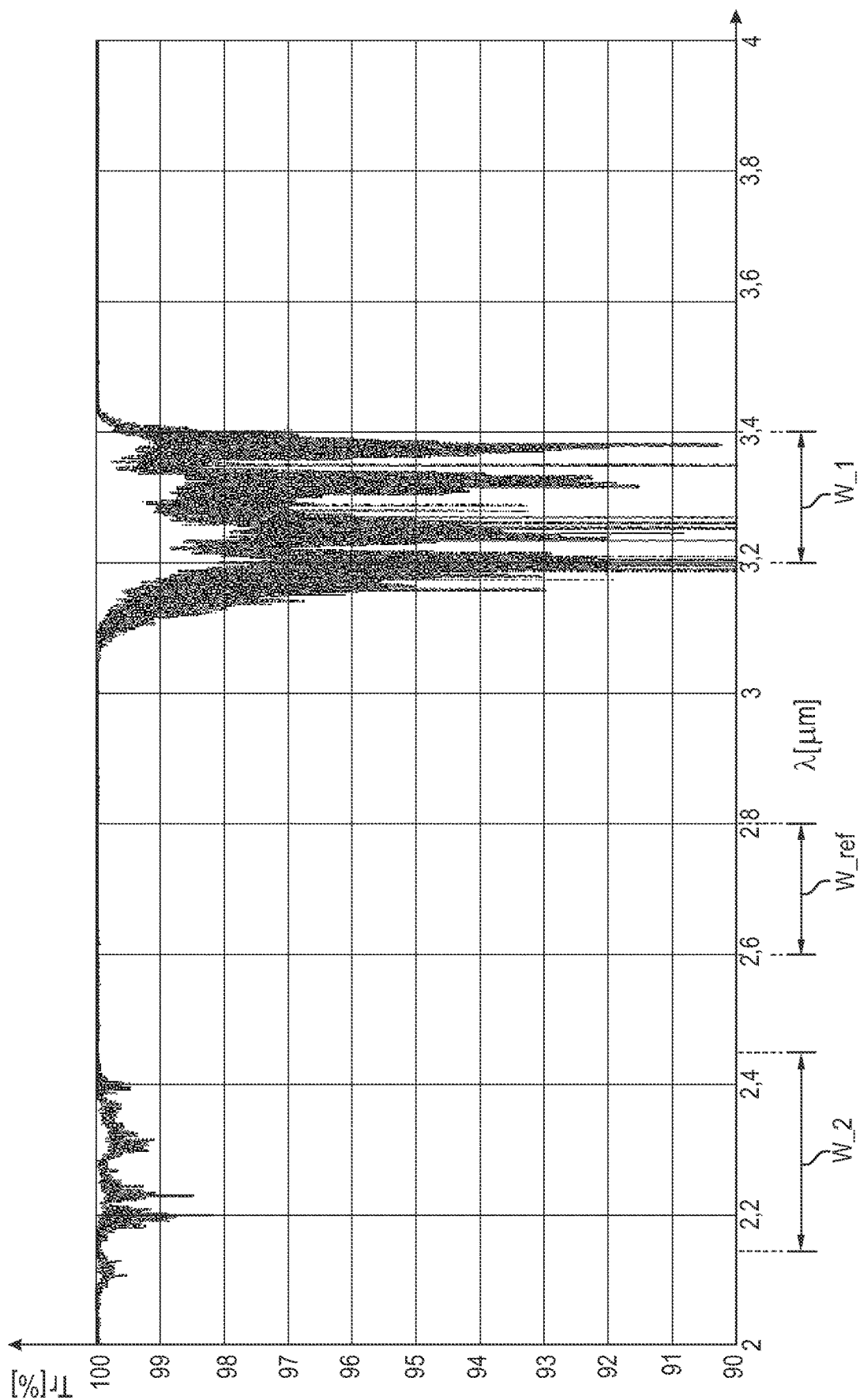
FIG. 7 is a graph showing the degree of transmission of ethylene of an average concentration as a function of the wavelength.

In particular,

FIG. 4 shows the degree of transmission Tr of methane of a relatively high concentration as a function of the wavelength λ, FIG. 5 shows the degree of transmission Tr of methane of an average concentration as a function of the wavelength λ, FIG. 6 shows the degree of transmission Tr of propane of an average concentration as a function of the wavelength λ, FIG. 7 shows the degree of transmission Tr of ethylene of an average concentration as a function of the wavelength λ, As can be seen in FIG. 4 through FIG. 7, these hydrocarbons absorb impinging electromagnetic radiation 50 essentially in two wavelength ranges, namely in a first wavelength range W_1 and in a second wavelength range W_2. A distance occurs between these two wavelength ranges W_1 and W_2. This distance is greater, by a multiple greater in the examples shown, than the length of the longer wavelength range W_1. The two wavelength ranges W_1 and W_2 may differ from target gas to target gas.

In the configuration of the gas detection device according to the present invention, it is known which target gas 60.1, 60.2 shall be detected and in what concentration range the concentration of this target gas 60.1, 60.2 is during the use. Therefore, these two wavelength ranges W_1 and W_2 are known before the use. The first wavelength range W_1 consists in the exemplary embodiment of longer wavelengths than the second wavelength area W_2. The two wavelength ranges W_1 and W_2 and a reference wavelength range W_ref are predefined, wherein the wavelength range W_ref has a respective distance to the first wavelength range and to the second wavelength range W_1, W_2 and in which the target gas to be detected absorbs practically no electromagnetic radiation 50. This reference wavelength range W_ref is likewise shown as an example in FIG. 4 through FIG. 7.

Figure 8:
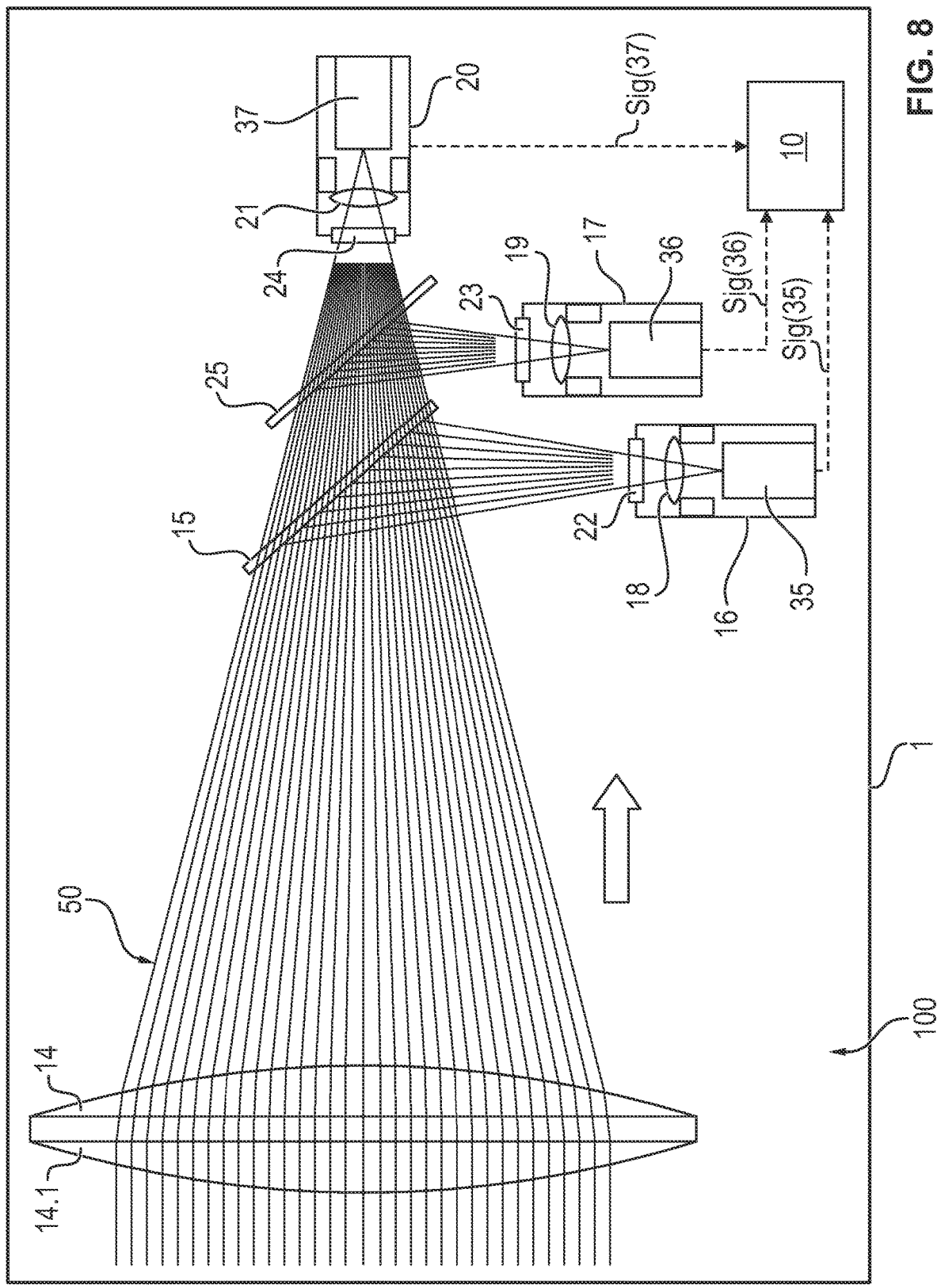
FIG. 8 is a schematic view showing the receiving unit according to a preferred embodiment of the gas detection device according to the present invention.

FIG. 8 shows a preferred embodiment of a receiving unit 100 of the gas detection device according to the present invention. Identical reference numbers have the same meaning as in FIG. 1 and FIG. 2. The transmitting unit 33 of the gas detection device according to the present invention may be configured just as shown in FIG. 1. The emitted electromagnetic radiation 50, in turn, penetrates the area 40 and impinges on the receiving unit 100 in the receiver-side housing 1.

The following components are arranged in this receiver-side housing 1:

a window 2 in the receiver-side housing 1 shields the receiver-side housing 1 from the area 40 and may be provided with heating elements 3 in a manner as shown in FIG. 2. The window 2 is permeable to electromagnetic radiation 50.

a planar-convex convergent lens 14, optionally a convex-planar convergent lens 14.1 upstream of the convergent lens 14, a front optical filter 15, a rear optical filter 25, a front detector 16 with a window 22, with a convergent lens 18 and with a photosensor 35, wherein the photosensor 35 acts as the first gas photosensor of the exemplary embodiment, a middle detector 17 with a window 23, with a convergent lens 19 and with a photosensor 36, wherein the photosensor 36 acts as the reference photosensor, a rear detector 20 with a window 24, with a convergent lens 21 and with a photosensor 37, wherein the photosensor 37 acts as the second gas photosensor, and a signal-processing analysis unit 10, which receives and automatically analyzes a respective signal Sig(35), Sig(36), Sig(37) from the three photosensors 35, 36, 37.

The designations "front," "middle" and "rear" refer to the direction of the incident radiation 50, i.e., from left to right in FIG. 8. The two filters 15 and 25 belong to the array of filters of the preferred embodiment according to FIG. 8. One advantage of this embodiment is that the preferred embodiment according to FIG. 8 has a relatively small expansion in an area at right angles to the direction, in which the electromagnetic radiation impinges on the array of filters 15, 25.

The convergent lens 14 and the optional convergent lens 14.1 are arranged in the receiver-side housing 1. These lenses 14, 14.1 are optionally heated. The radiation source 31 also preferably comprises at least one lens 32 (FIG. 1), which is heated in one embodiment at least from time to time by a heating element, in order to prevent the condensation of water. The lens or each lens used may be shaped, for example, with additional facets, or be ground or pressed.

In the example being shown, the analysis unit 10 is arranged in the receiver-side housing 1. It is also possible that the analysis unit 10 is arranged outside of the receiver-side housing 1, for example, in an area that is at a distance in space and is secured. The signals Sig(35), Sig(36) and Sig(37) are transmitted from the detectors 16, 17, 20 to the analysis unit 10 in a cabled manner or by radio waves.

It is also possible that the analysis unit 10 is additionally used as a control device, which actuates the radiation source 31 and, for example, causes the radiation source 31 to emit electromagnetic radiation 50 in a pulsed manner (emit pulsed electromagnetic radiation 50).

The front optical filter 15 reflects a portion of the impinging electromagnetic radiation 50 towards the front detector 16 as a function of the wavelength λ and lets the rest of the radiation 50 pass through. The rear optical filter 25 reflects a portion of the impinging radiation 50, which has passed through the front detector 15, towards the middle detector 17 as a function of the wavelength λ and lets the rest of the radiation pass to the rear detector 20. In the example shown, the optical filters 15 and 25 deflect a portion of the radiation by 90° each. Other deflection angles are likewise possible.

In one implementation of the exemplary embodiment, the range between 3.2 µm and 3.4 µm acts as the first wavelength range W_1, the range between 2.3 µm and 2.4 µm acts as the second wavelength range W_2 and the range between 2.05 µm and 2.15 µm acts as the reference wavelength range W_ref. If methane in an average concentration is present in the area 40, then the methane attenuates the electromagnetic radiation 50 in the first wavelength range W_1 and in the second wavelength range W_2 in a detectable manner, but not in the reference wavelength range W_ref, cf. FIG. 5. The reference wavelength range W_ref may also be arranged between the two wavelength ranges W_1 and W_2 for the detection of methane.

As can be seen in FIG. 6, propane also significantly attenuates the radiation 50 in this first wavelength range W_1 and in this second wavelength range W_2, so that in many cases the gas detection device can be used for the detection of methane and, unchanged, also for the detection of propane. In another embodiment, other wavelength ranges W_1 and W_2 are predefined, cf. FIG. 6. If the gas detection device shall detect ethylene, then a different reference wavelength range W_ref is preferably predefined, which can be seen in FIG. 7, namely a range from 2.6 µm to 2.8 µm.

The front optical filter 15 reflects electromagnetic radiation 50 in the first wavelength range W_1 and transmits electromagnetic radiation 50 (lets this radiation pass through) outside of the first wavelength range W_1, cf. FIG. 8. The front detector 16 is arranged such that reflected radiation 50 passes through the window 22 and the convergent lens 18 and then impinges on the photosensor 35 (first gas photosensor). Transmitted electromagnetic radiation 50, i.e., radiation 50 outside of the first wavelength range W_1, impinges on the second optical filter 25. The second optical filter 25 transmits radiation 50 in the second wavelength range W_2 and reflects radiation outside of the second wavelength range W_2. The transmitted radiation 50 impinges on the rear detector 20, passes through the window 24 and the convergent lens 21 and then impinges on the photosensor 37 (second gas photosensor). The reflected radiation 50 impinges on the middle detector 17, passes through the window 23 and through the convergent lens 19 and then impinges on the photosensor 36 (reference photosensor). In this embodiment the windows 22, 23, 24 have a protective function and ideally do not absorb any radiation.

In this preferred embodiment electromagnetic radiation 50 in the first wavelength range W_1 is then preferably reflected only once by an optical filter (filter 15) before electromagnetic radiation impinges on a photosensor (namely on the photosensor 35 of the front detector 16, first photosensor). Radiation 50 in the second wavelength range W_2 passes through the array of filters (filters 15 and 25), before it impinges on a photosensor (namely on the photosensor 37 of the rear detector 20, second photosensor). During the passage through two filters 15, 25, the radiation 50 is inevitably attenuated more intensely than during the passage through only one filter 15 or during the reflection by the filter 15. Therefore, it is advantageous that the second wavelength range W_2, to which the photosensor 37 of the rear detector 20 is sensitive, consists of shorter wavelengths λ than the first wavelength range W_2, to which the photosensor 35 of the front detector 36 is sensitive thanks to the array of filters 15, 25. On the one hand, the frequency f is generally known and thus the shorter the wavelength λ is, the greater is the intensity of electromagnetic radiation 50. Another reason why the arrangement shown in FIG. 8 is advantageous is as follows: The radiation 50 on the path from the radiation source 31 in the exemplary embodiment penetrates through the area 40 to the detectors 16, 17, 20 in the receiver-side housing 1 in addition to the lens 32 of the radiation source 31 and the convergent lens 14 in the receiver-side housing 1. Especially when the lens 32 and/or the convergent lens 14 is shaped or ground or pressed, these lenses 32, 14 also inevitably absorb radiation 50, doing so in an especially intensified manner in a wavelength range above 2.5 µm.

The photosensors 35, 36, 37 of the three detectors 16, 20, 17 generate each an electrical signal Sig(35), Sig(36), Sig(37), especially as a function of the intensity of impinging electromagnetic radiation 50. The greater the generated signal value is, the greater is the intensity of the impinging radiation 50. The array of filters with the two optical filters 15 and 25 distributes the impinging radiation 50 as a function of the wavelength λ onto the three detectors 16, 20, 17 and thus also onto the three photosensors 35, 36, 37. The signals Sig(35), Sig(36), Sig(37) thereof are transmitted to the analysis unit 10.

The photosensor 35 of the front detector 16 comprises, for example, a type II semiconductor diode, e.g., InAsSb. A photosensor 35 configured in this manner is capable of responding sufficiently rapidly to the short pulsed rays of the radiation 50 that the radiation source 31 emits. Furthermore, a photosensor 36 configured in this manner has a sufficiently high spectral sensitivity D* in the range of about 3.3 µm. The photosensor 35 of the front detector 16 responds in many cases to the absence of methane as the target gas to be detected, which attenuates or even absorbs radiation in the wavelength rage greater than 3 µm, cf. FIG. 4 and FIG. 5.

In a typical application in the range of 0.5 LELm to 8 LELm methane, 22,000 to 352,000 molecules of methane are located within the optical path length to be monitored in the area 40. Because of the high absorption of alkanes in the range of about 3.3 µm, this high number of molecules is sufficient to let the photosensor 35 of the front detector 16 respond as a sensor.

In one embodiment, the photosensor 36 of the middle detector 17 and/or the photosensor 37 of the rear detector 20 are each configured as an InGaAs photosensor. An InGaAs photosensor is capable of readily detecting attenuations of wavelengths up to a wavelength of 2.6 µm. It is also possible to configure the photosensor 36 of the middle detector 17 and/or the photosensor 37 of the rear detector 20 just like the photosensor 35 of the front detector 16 likewise as a respective InAsSb detector.

In one embodiment, the two photosensors 36 and 37 have the highest sensitivity in the same wavelength range of 2.0 µm to 2.5 µm and have a similar configuration. It is also possible that these two photosensors 36 and 37 have their respective highest sensitivity in different wavelength ranges.

Figure 9:
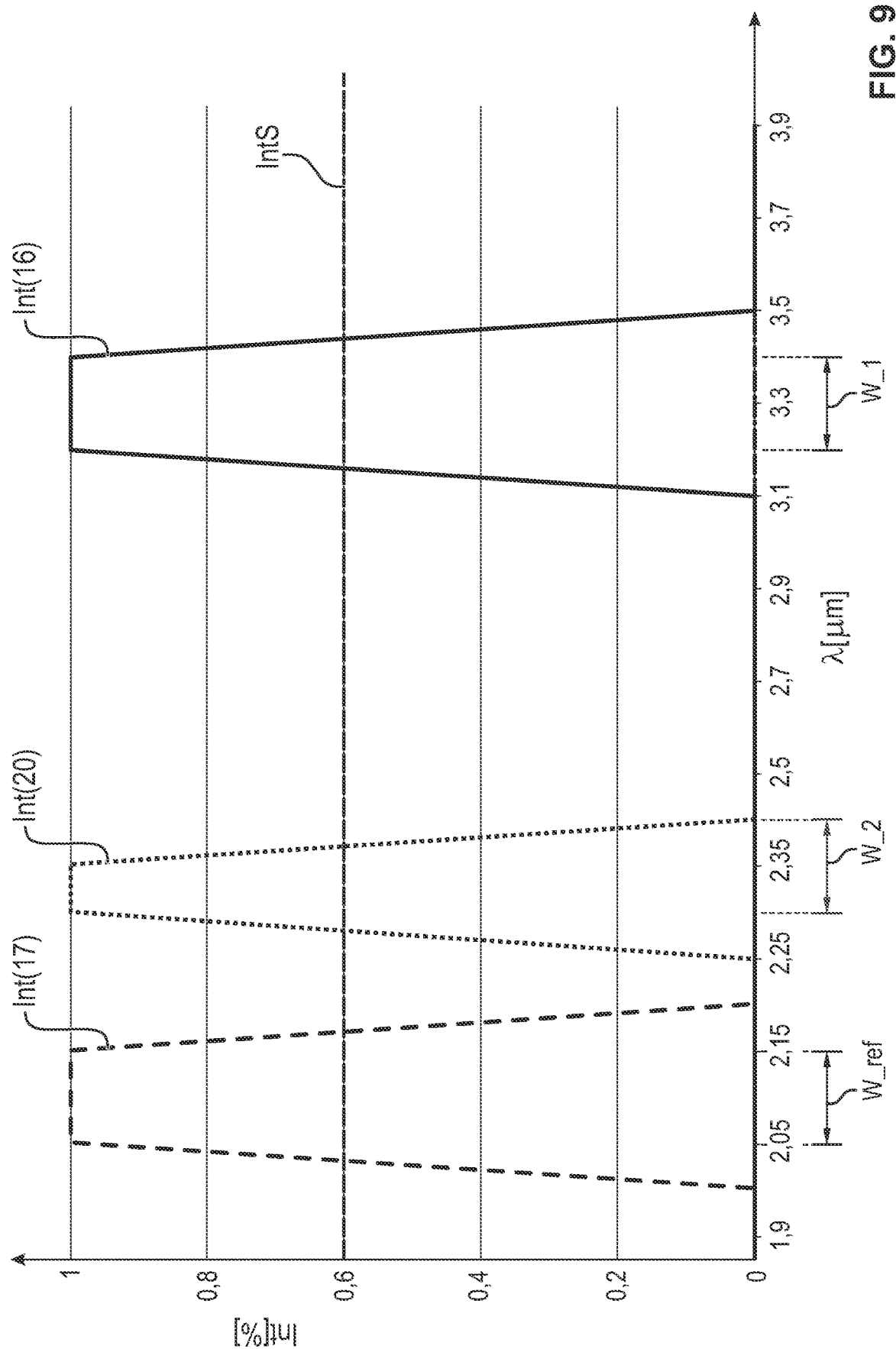
FIG. 9 is a graph showing the relative strength of signals, which the three photosensors generate, as a function of the wavelength, wherein neither methane nor a contamination is present.

FIG. 9 shows the respective relative signal strength Int(17), Int(16) and Int(20) of the three photosensors 35, 36, 37 for the ideal case that neither a gas, which attenuates electromagnetic radiation 50, especially not the target gas, nor a contamination is present in the area 40 and therefore the electromagnetic radiation 50 is not relevantly attenuated in the area 40 The dependence of the relative signal strength Int on the wavelength λ is hence achieved exclusively by the array of filters 15, 25 and by the construction of the three photosensors 35, 36, 37. The wavelength λ of the impinging radiation 50 in a range between 1.9 µm and 3.9 µm is, in turn, plotted on the x axis, and the relative signal strength Int as a percentage of the maximum achievable signal strength in % is plotted on the y axis. The maximum achievable signal strength may be different from one photosensor to the next, especially when at least two photosensors of different configurations are used.

In addition, a predefined intensity limit IntS of, e.g., 0.6=60% is plotted. It can be seen that the photosensor 36 of the reference detector 17 generates a signal strength Int(17), which is above the intensity limit IntS only in the reference wavelength range W_ref and drops sharply outside of this range. The photosensor 37 of the rear detector 20 generates a signal strength Int(20), which is above the intensity limit IntS only in the second wavelength range W_2, the photosensor 36 of the middle detector 16 generates a signal strength Int(16), which is above the intensity limit IntS only in the first wavelength range W_1. In the example being shown, the same intensity limit IntS=0.6 is predefined for all three photosensors 35, 36, 37. It is also possible to predefine two or even three different intensity limits.

In one embodiment, the intensity limit or each intensity limit IntS is set during a calibration at a respective value, which yields a good compromise between the two requirements, on the one hand, to detect the target gas with certainty and, on the other hand, to generate only a small number of false alarms.

Figure 10:
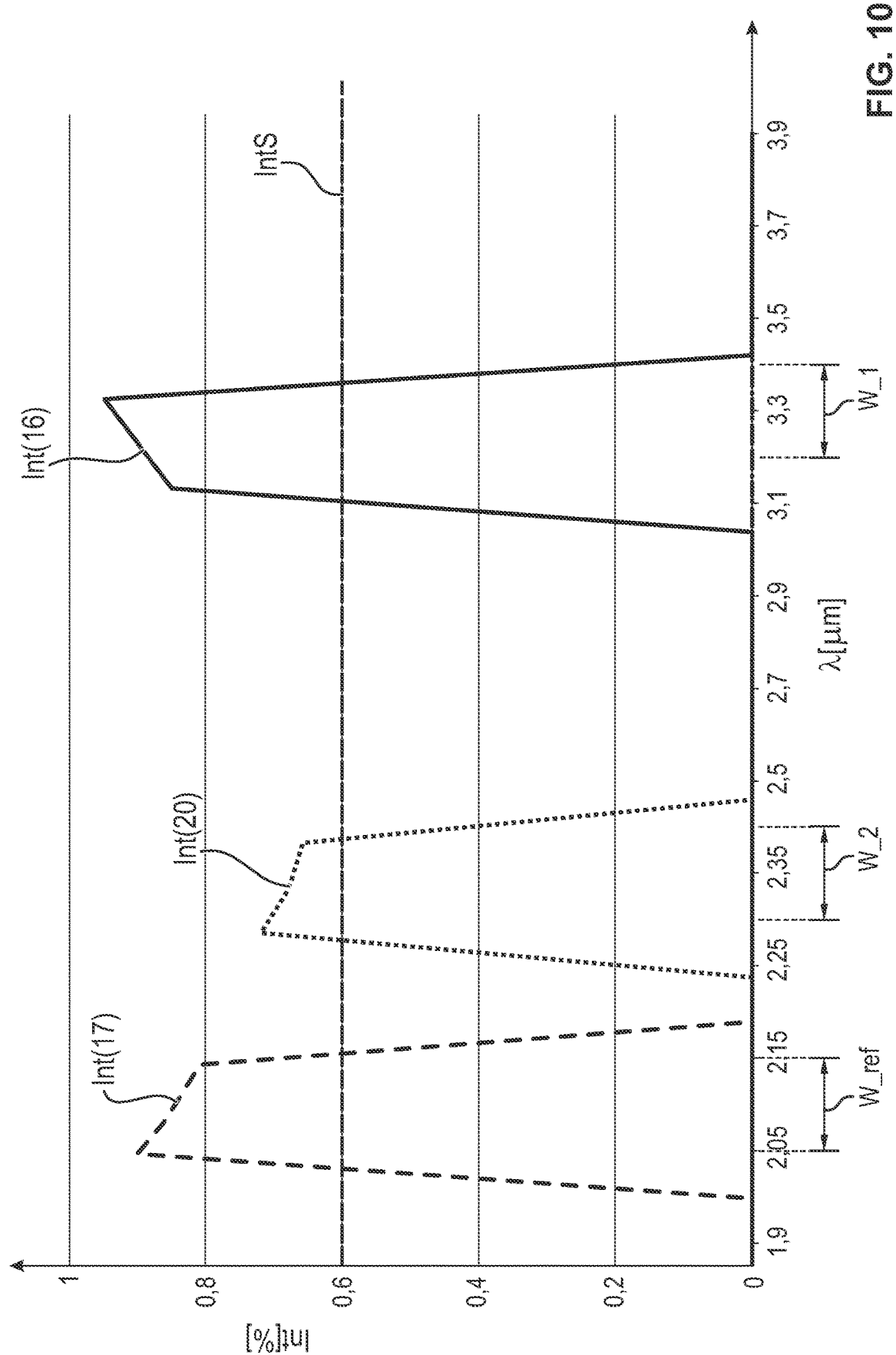
FIG. 10 is a graph similar to FIG. 9, wherein no methane is present, but a first kind of a contamination is present.
Figure 11:
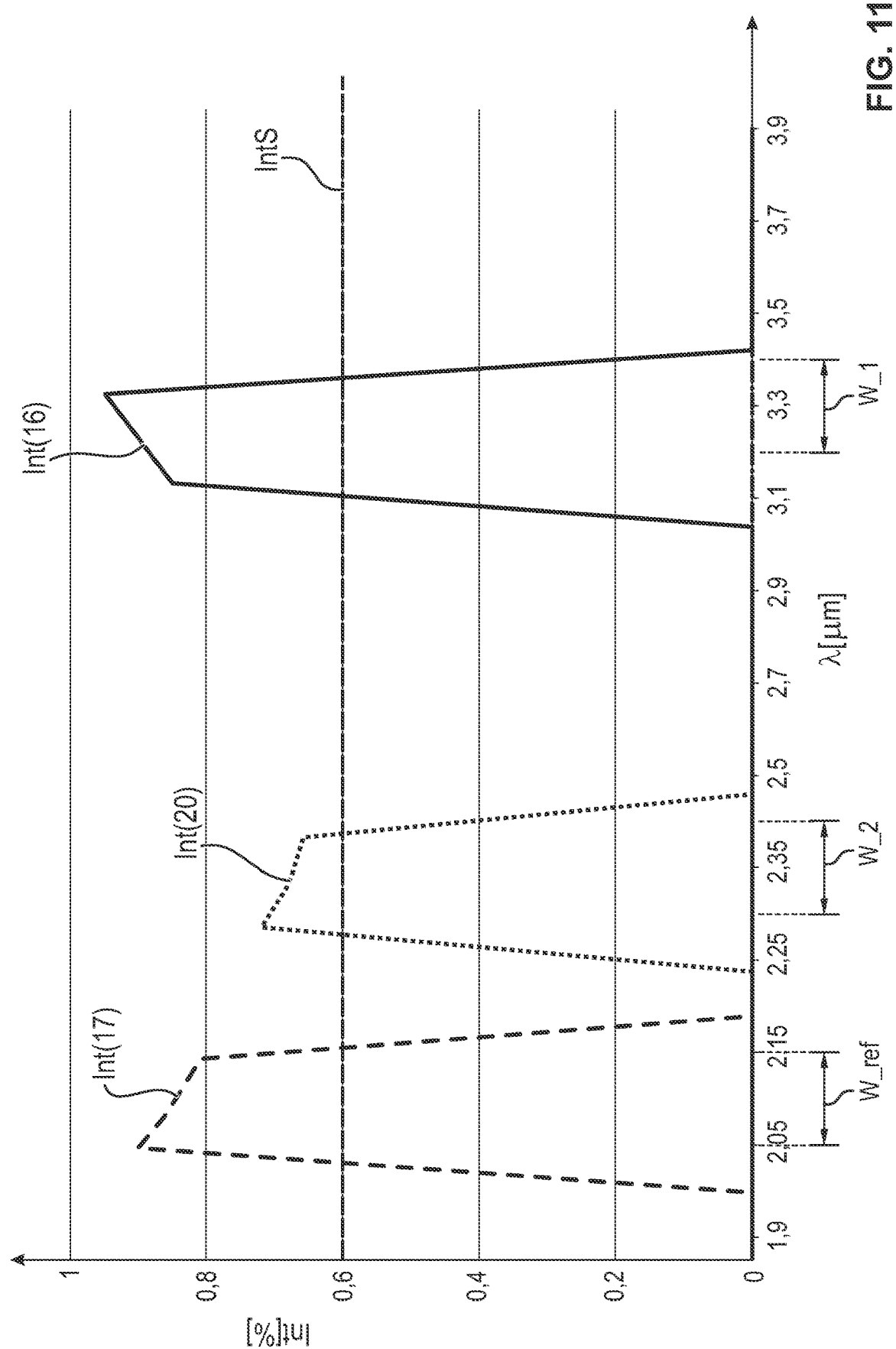
FIG. 11 is a graph similar to FIG. 9, wherein no methane is present, but a second kind of a contamination is present.

FIG. 10 and FIG. 11 show a variation of the diagram of FIG. 9. Also in this example of FIG. 10 and FIG. 11, no gas, which attenuates electromagnetic radiation 50, is present in the area 40 being monitored, but two different kinds of contamination, for example, because of liquid droplets or dust particles are present. It can be seen that the photosensors 35, 36, 37 of the detectors 16, 20, 17 no longer yield the respective maximum signal strength. The relative signal strength Int is only within the respective wavelength range above the intensity limit IntS in these situations as well.

Figure 12:
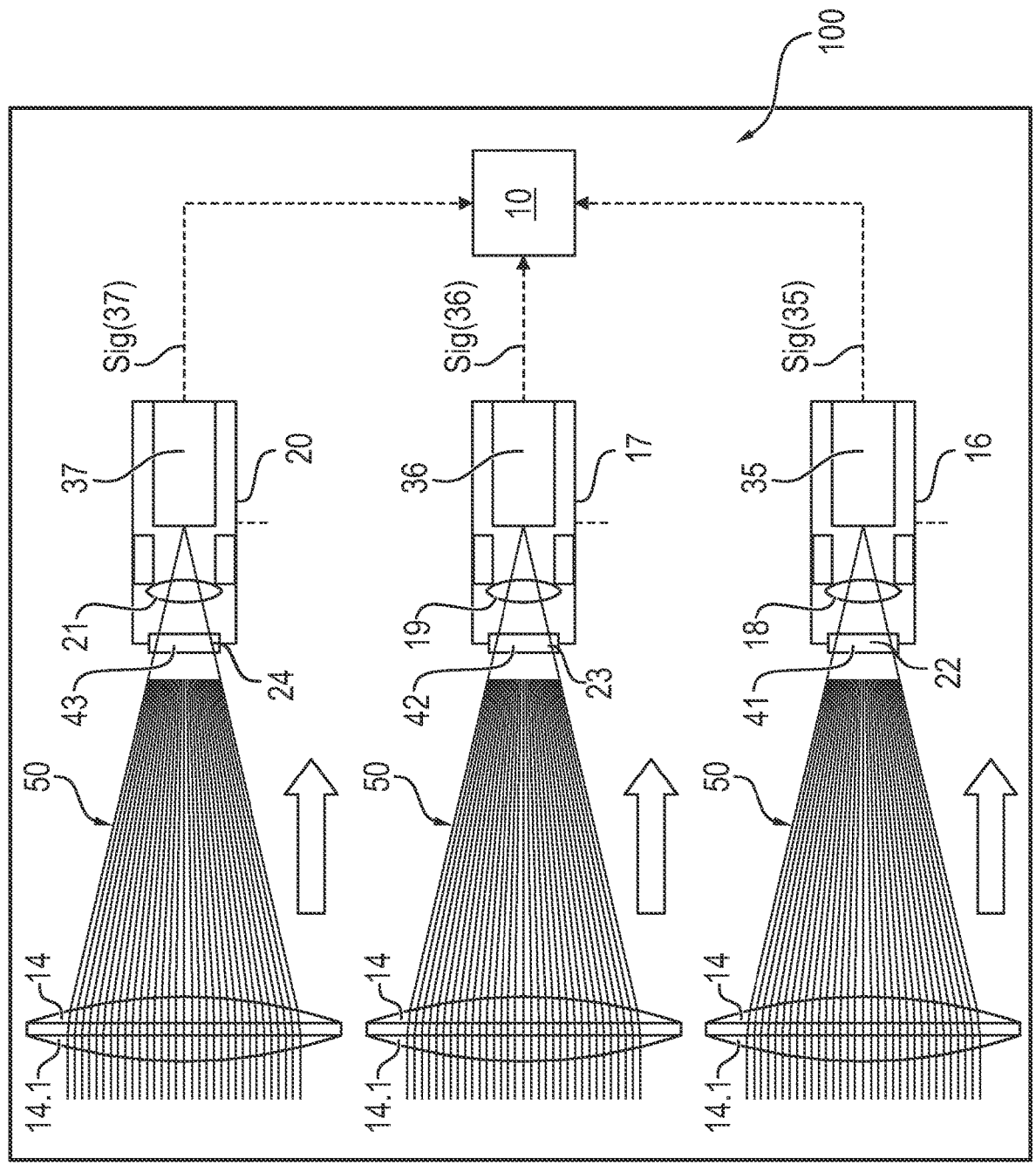
FIG. 12 is a schematic view showing the receiving unit according to another embodiment of the gas detection device according to the present invention.

FIG. 12 shows an alternative configuration of the gas detection device according to the present invention. Identical reference numbers have the same meaning as in FIG. 8.

The three detectors 16, 17 and 20 are arranged parallel to one another according to this alternative configuration. Nevertheless, the designations "front detector 16," "middle detector 17" and "rear detector 20" are maintained. One advantage of the configuration according to FIG. 12 is that the radiation 50 must pass through only one filter regardless of the wavelength λ, until it reaches a photosensor 35, 36, 37. In particular, the photosensor 35, 36, 37 does not need to measure the intensity of an already reflected radiation 50.

By contrast to the configuration according to FIG. 8, the three windows 21, 22, 23 are configured as detector filters 41, 42, 43. In the configuration according to FIG. 12, the three detector filters 41, 42, 43 belong to the array of filters.

The detector filter 41 of the front detector 16 lets only radiation 50 in the first wavelength range W_1 pass through (transmits this radiation 50) and absorbs or reflects the radiation 50 outside of the first wavelength range W_1. The detector filter 42 of the middle detector 17 lets only radiation 50 in the reference wavelength range W_ref pass through, the detector filter of the rear detector 20 lets only radiation 50 in the second wavelength range W_2 pass through.

Electromagnetic radiation 50, which has penetrated the area 40, impinges on all three detectors 16, 17 and 20. The radiation 50, which impinges on the front detector 16 and is in the first wavelength range W_1, passes through the first detector filter 41 and through the convergent lens 18 and reaches the photosensor 35. The radiation 50, which impinges on the middle detector 17 and is in the reference wavelength range W_ref, passes through the second detector filter 42 and through the convergent lens 19 and reaches the photosensor 36. The radiation 50, which impinges on the rear detector 20 and is in the second wavelength range W_2, passes through the third detector filter 43 and through the convergent lens 21 and reaches the photosensor 37. The signals Sig(35), Sig(36), Sig(37) of the three photosensors 35, 36, 37 are, in turn, transmitted to the analysis unit 10.

The alternative configuration shown in FIG. 12—with corresponding configuration of the three detector filters 41, 42, 43—also achieves the relative signal strengths Int(16), Int(17) and Int(20), which are shown in FIG. 9 through FIG. 11, in one embodiment.

An exemplary mode of operation of the signal-processing analysis unit 10 is described below. This mode of operation can especially be applied to a receiving unit 100 according to FIG. 8 and to a receiving unit 100 according to FIG. 12.

As was already mentioned, the analysis unit 10 receives a respective value for the signals Sig(35), Sig(36), Sig(37) from the three photosensors 35, 36, 37 at each scanning time during a disturbance-free operation. Of course, these values may have been processed beforehand. According to the present invention, the analysis unit 10 carries out three respective pair comparisons at each scanning time, wherein the respective signal values from two photosensors 36, 37; 36, 35, 37, 35 are compared with one another for the same scanning time during each pair comparison. In the exemplary embodiment, the analysis unit calculates at each scanning time three respective quotients Q1, Q2, Q3, namely $Q1 := \text{Int}(36)/\text{Int}(37),$ $Q2 := \text{Int}(36)/\text{Int}(35)$ and $Q3 := \text{Int}(37)/\text{Int}(35).$ Int(35), Int(36) and Int(37) are the relative signal strengths of the values of the signals Sig(35), Sig(36), Sig(37) from the three photosensors 35, 36, 37.

The following description pertains to methane as the target gas to be detected. If methane with a concentration above the detection limit is present in the area 40 to be monitored, then this leads to the following change compared with a situation without methane in the area 40, cf. FIG. 4 and especially FIG. 5:

Radiation 50 in the first wavelength range W_1 (3.2 μm to 3.4 μm) is attenuated considerably, radiation in the second wavelength range W_2 (2.3 μm to 2.4 μm) is attenuated measurably, and radiation in the reference wavelength range W_ref (2.05 μm to 2.15 μm) is ideally not attenuated at all.

Thanks to the array of filters, the photosensor 35 of the front detector 16 (first gas photosensor) is only sensitive in the first wavelength range W_1, the photosensor 37 of the rear detector 20 (second gas photosensor) is only sensitive in the second wavelength range W_2 and the photosensor 36 of the middle detector 17 (reference photosensor) is sensitive only in the reference wavelength range W_ref, cf. FIG. 9.

The first quotient Q1 and the second quotient Q2 are larger, because the respective denominator Int(20) or Int(16) is smaller; however, the numerator Int(17) ideally remains the same.

The third quotient Q3 ideally remains the same.

Absolute signal strengths may also be used instead of the relative signal strengths Int(16), Int(17), Int(20).

The three quotients Q1, Q2 and Q3 depend on the concentration of methane in the area 40 and in addition on possible contaminations, cf. FIG. 10 and FIG. 11, and frequently also on aging. Therefore, the gas detection device is preferably calibrated beforehand. This calibration can be carried out again during the use, also as needed at regular time intervals and/or as a function of the previous use of the gas detection device.

During each calibration, the gas detection device is used on a trial basis in the area 40 to be monitored or in a reference area, which is sufficiently similar to the area 40 to be monitored. The following two situations are established in the area 40 used during the calibration or in the reference area:

Methane, but no relevant contamination, is present in the area 40.

Neither methane nor a relevant contamination is present in the area 40.

Optionally, at least one of the following additional situations is established:

Methane of an average concentration and a contamination are present in the area 40.

No methane, but a contamination is present in the area 40.

Methane of a relatively low or of a relatively high concentration is present in the area 40.

For each situation, which is established during the calibration, the respective three quotients Q1, Q2, Q3 defined above are calculated. A plurality of measurements are preferably carried out in case of each situation in order to eliminate unavoidable process noise and measurement noise up to a certain extent by averaging or formation of the median. The three quotients Q1, Q2 and Q3 of a measurement together form a triple in a three-dimensional coordinate system, preferably in a cartesian coordinate system. For each situation, which is established during the calibration, at least one triple in this coordinate system is thus calculated, and a plurality of triples in case of a plurality of measurements. Some of these triples belong to a situation with methane, and the others belong to a situation without methane. As a result, two partial quantities are formed in the three-dimensional coordinate system, namely a first partial quantity with triples in case of the presence of methane and a second partial quantity with triples in case of the absence of methane. An area between these two partial quantities is set by calculation. This area may be flat or curved. The area divides the three-dimensional coordinate system into two partial areas, wherein one partial area denotes the presence and one partial area denotes the absence of methane.

During use of the gas detection device according to the present invention, the analysis unit 10 again calculates at each scanning time the three quotients Q1, Q2 and Q3, as a result of which a triple is calculated. The analysis unit 10 automatically determines whether this triple falls in the partial area of the coordinate system, which denotes the presence of methane, or in the other partial area. If a triple falls in the partial area for the presence of methane, then the analysis unit 10 has detected the target gas methane. The analysis unit then preferably triggers the step that an alarm is generated in a form perceptible by a person and/or a message is sent to a receiver and the receiver outputs the message in a form perceptible by a person. Preferably the receiver is positioned at a spaced distance from the receiving unit 100.

The period between two immediately consecutive scanning times is preferably so long that radiation 50 in the entire wavelength of 2 μm to 4 μm is emitted in this period and penetrates the area 40. If the emitted radiation 50 varies with time, signal values from the photosensors 35, 36, 37 are preferably averaged in order to cover the entire wavelength range of 2 μm to 4 μm.

Instead of the quotient, a different value, which depends in a suitable manner on the relative or absolute signal strengths of the two photosensors, may also be calculated during a pair comparison.

While specific embodiments of the invention have been shown and described in detail to illustrate the application of the principles of the invention, it will be understood that the invention may be embodied otherwise without departing from such principles.

LIST OF REFERENCE CHARACTERS

1 Receiver-side housing of the receiving unit 100; it accommodates the convergent lenses 14, 14.1, the optical filters 15, 25, the detectors 16, 17, 20 and optionally the analysis unit 10
2 Window in the receiver-side housing 1; it shields the receiver-side housing 1 from the area 40; it is permeable to electromagnetic radiation 50
3 Heating elements for the window 2
4 Coated convergent lens; it has a planar surface and a convex surface
5 Beam splitter or color filter
6 First detector; it comprises the optical detector filter 8
7 Second detector; it comprises the optical detector filter 9
8 Optical detector filter of the first detector 6
9 Optical detector filter of the second detector 7
10 Signal-processing analysis unit; it receives signals from the photosensors 35, 36,37 of the detectors 16, 17, 20 and it determines whether or not a target gas to be detected is present in the area 40
11 Receiver-side housing of the receiving unit 1000
12 Signal-processing analysis unit
14 Convergent lens of the gas detection device according to the present invention, it is arranged in the receiver-side housing 1
14.1 Optional convex-planar convergent lens in front of the convergent lens 14
15 Front optical filter of the gas detection device according to the present invention; it is configured as a broadband filter; it reflects radiation 50 in the first wavelength range W_1 and it transmits the remaining radiation 50
16 Front detector (first gas detector) of the gas detection device according to the present invention; it comprises the photosensor 35 and the convergent lens 18 as well as the window 22 or the detector filter 41
17 Middle detector (reference gas detector) of the gas detection device according to the present invention; it comprises the photosensor 36 and the convergent lens 18 as well as the window 23 or the detector filter 42
18 Convergent lens of the front detector 16
19 Convergent lens of the middle detector 17
20 Rear detector (second gas detector) of the gas detection device according to the present invention; it comprises the photosensor 37 and the convergent lens 21 as well as the window 24 or the detector filter 43
21 Convergent lens of the rear detector 20
22 Window of the front detector 16; it is permeable to radiation 50
23 Window of the middle detector 17; it is permeable to radiation 50

24 Window of the rear detector 20; it is permeable to radiation 50

25 Rear optical filter of the gas detection device according to the present invention; it transmits radiation 50 in the second wavelength range W_2 and it reflects the remaining radiation 50

30 Transmitter-side housing of the transmitting unit 33; it accommodates the radiation source 31 and the convergent lens 32

31 Radiation source of the transmitting unit 33; it emits electromagnetic radiation 50; it is arranged in the transmitter-side housing 30

32 Convergent lens in the transmitter-side housing 30

33 Transmitting unit of the gas detection housing; it comprises the radiation source 31, the convergent lens 32 under the transmitter-side housing 30

35 Photosensor of the front detector 16; it is reached only by radiation 50 in the first wavelength range W_1; it acts as the first gas photosensor; it has a high spectral sensitivity D* in the range of 3 m to 3.5 m 36 Photosensor of the middle detector 17; it is reached only by radiation 50 in the reference wavelength range W_ref; it acts as the reference photosensor; it has a high spectral sensitivity D* in the range of 2 m to 2.5 m 37 Photosensor of the rear detector 20; it is reached only by radiation 50 in the second wavelength range W_2; it acts as the second gas photosensor; it has a high spectral sensitivity D* in the range of 2 m to 2.5 m 40 Area to be monitored; it is arranged between the housings 30 and 1; it may contain a target gas 60.1, 60.2

41 Detector filter of the front detector 16; it lets only radiation 50 in the first wavelength range W_1 pass through 42 Detector filter of the middle detector 17; it lets only radiation 50 in the reference wavelength range W_ref pass through 43 Detector filter of the rear detector 20; it lets only radiation 50 in the second wavelength range W_2 pass through 50 Electromagnetic radiation, which is emitted by the radiation source 31, penetrates the area 40 to be monitored and impinges on the receiver-side housing 1

60.1, 60.2 Target gas to be detected in the area 40 to be monitored; it attenuates electromagnetic radiation in the two wavelength ranges W_1 and W_2

100 Receiving unit of the gas detection device according to the present invention; it comprises the housing 1, the convergent lenses 14, 14.1, the optical filters 15, 25, the detectors 16, 17, 20 and optionally the analysis unit 10

1000 Receiving unit of the gas detection device according to FIG. 2

Int(16) Relative signal strength which the photosensor 36 of the front detector 16 achieves Int(17) Relative signal strength which the photosensor 35 of the middle detector 17 achieves Int(20) Relative signal strength which the photosensor 37 of the rear detector 20 achieves IntS Predefined intensity limit Wavelength in [μm] of the electromagnetic radiation 50

Sig(35) Signal from the photosensor 35; it depends on the intensity of impinging radiation 50

Sig(36) Signal from the photosensor 36; it depends on the intensity of impinging radiation 50

Sig(37) Signal from the photosensor 37; it depends on the intensity of impinging radiation 50

Tr Relative degree of transmission in percent

W_1 First wavelength range, the range between 3.2 m and 3.4 m for methane

W_2 Second wavelength range, the range between 2.3 m and 2.4 m for methane

W_ref Reference wavelength range, the range between 2.05 m and 2.15 m for methane

What is claimed is:

1. A gas detection device for monitoring an area for a target gas to be detected, the gas detection device comprising:
a radiation source configured to emit electromagnetic radiation such that at least a portion of the emitted radiation penetrates the area to be monitored;
a first gas photosensor configured to generate a first gas photosensor signal as a function of a first gas photosensor impinging electromagnetic radiation intensity;
a second gas photosensor configured to generate a second gas photosensor signal as a function of a second gas photosensor impinging electromagnetic radiation intensity;
a reference photosensor configured to generate a reference photosensor signal as a function of a reference photosensor impinging electromagnetic radiation intensity;
an array of filters, wherein the radiation source is configured to emit the electromagnetic radiation such that at least a portion of the emitted radiation impinges on the array of filters and the array of filters is configured to distribute impinging radiation as a function of wavelength onto the photosensors and the array of filters is configured and positioned in relation to the photosensors such that the distribution of impinging radiation, in a state with no gas attenuating the electromagnetic radiation present in the area to be monitored, comprises:
a first radiation portion in a predefined first wavelength range, which first radiation portion impinges on the first gas photosensor with an intensity above a predefined first radiation intensity limit and radiation outside of the first wavelength range does not impinge on the first gas photosensor or impinges on the first gas photosensor with an intensity below the predefined first radiation intensity limit,
a second radiation portion in a predefined second wavelength range, which second radiation portion impinges on the second gas photosensor with an intensity above a predefined second radiation intensity limit and radiation outside of the second wavelength range does not impinge on the second gas photosensor or impinges on the second gas photosensor with an intensity below the predefined second radiation intensity limit; and
a reference radiation portion in a predefined reference wavelength range, which reference radiation portion impinges on the reference photosensor with an intensity above a predefined reference radiation intensity limit, and radiation in the first wavelength range and radiation in the second wavelength range does not impinge on the reference photosensor or impinges on the reference photosensor with an intensity below the reference radiation intensity limit, wherein there is no overlap between two of the first wavelength range, the second wavelength range and the reference wavelength range; and
an analysis unit configured to compare the first gas photosensor signal, the second gas photosensor signal and the reference photosensor signal with one another based on the analysis unit being configured to: carry out a pair comparison for each of the first gas photosensor signal, the second gas photosensor signal and the reference photosensor signal comprising three pair comparisons of two photosensors including comparing the first gas photosensor signal with the second gas photosensor signal, comparing the second gas photosensor signal and the reference photosensor signal and comparing the first gas photosensor signal and the reference photosensor signal and as a function of the three pair comparison:
to determine whether or not the target gas to be detected is present in the area to be monitored; or
to determine a concentration indication of the target gas in the area to be monitored; or
to determine whether or not the target gas to be detected is present in the area to be monitored and to determine a concentration indication of the target gas in the area to be monitored.

2. A gas detection device in accordance with claim 1, wherein the analysis unit compares the first gas photosensor signal, the second gas photosensor signal and the reference photosensor signal with one another based on the analysis unit being configured to:
carry out a pair comparison for each of the first gas photosensor signal, the second gas photosensor signal and the reference photosensor signal comprising three pair comparisons of two photosensors including comparing the first gas photosensor signal with the second gas photosensor signal, comparing the second gas photosensor signal and the reference photosensor signal and comparing the first gas photosensor signal and the reference photosensor signal; and
as a function of a result of the three pair comparisons:
to determine whether or not the target gas to be detected is present in the area to be monitored; or
to determine an indication of a concentration of the target gas in the area to be monitored; or
to determine whether or not the target gas to be detected is present in the area to be monitored and to determine an indication of a concentration of the target gas in the area to be monitored.

3. A gas detection device in accordance with claim 2, wherein:
for the pair comparison for each of the first gas photosensor signal, the second gas photosensor signal and the reference photosensor signal the analysis unit is configured to calculate a respective quantity in each pair comparison; and
each quantity depends on a quotient of two signal values of the two photosensors of the pair comparison.

4. A gas detection device in accordance with claim 3, wherein each quantity is equal to the quotient of two signal values of the two photosensors of the pair comparison.

5. A gas detection device in accordance with claim 1, wherein:
the analysis unit is configured to determine whether or not the target gas to be detected is present in the area to be monitored or to determine an indicator of the concentration of the target gas or to determine whether or not the target gas to be detected is present in the area to be monitored and to determine an indicator of the concentration of the target gas as a function of the result of the comparison of the three signals and as a function of a predefined reference comparison result, which describes an expected comparison result in case of a state free from a gas which gas would otherwise attenuate electromagnetic radiation;
the analysis unit is configured to determine that the target gas is present, when the first gas photosensor signal and/or the second gas photosensor signal is attenuated more intensely than the reference comparison result in relation to the reference photosensor signal.

6. A gas detection device in accordance with claim 1, wherein the array of filters comprises a first optical filter and a second optical filter, the first optical filter is configured to reflect electromagnetic radiation in the first wavelength range and to transmit electromagnetic radiation outside of the first wavelength range, and radiation reflected by the first optical filter impinges on the first gas photosensor and radiation transmitted by the first optical filter impinges on the second optical filter; and
wherein:
the second optical filter is configured to transmit electromagnetic radiation in the second wavelength range and to reflect electromagnetic radiation outside of the second wavelength range and radiation reflected by the second optical filter impinges on the reference photosensor and radiation transmitted by the second optical filter impinges on the second gas photosensor; or
the second optical filter is configured to reflect electromagnetic radiation in the second wavelength range and to transmit electromagnetic radiation outside of the second wavelength range, and radiation transmitted by the second optical filter impinges on the reference photosensor and radiation reflected by the second optical filter impinges on the second gas photosensor.

7. A gas detection device in accordance with claim 5, wherein the first wavelength range is comprised of longer wavelengths than the second wavelength range.

8. A gas detection device in accordance with claim 1, wherein the array of filters comprises:
a first detector filter;
a second detector filter; and
a reference detector filter, wherein:
the first detector filter, the second detector filter and the reference detector filter are arranged parallel to one another such that the electromagnetic radiation, which penetrates the area to be monitored, impinges on each of the first detector filter, the second detector filter and the reference detector filter;
the detector filters and the photosensors are arranged such that electromagnetic radiation that penetrates the first detector filter impinges on the first gas photosensor, electromagnetic radiation that penetrates the second detector filter impinges on the second gas photosensor and electromagnetic radiation that penetrates the reference detector filter impinges on the reference detector;
the first detector filter is configured to transmit first radiation portion and to absorb or to reflect the remaining portion of the radiation;
the second detector filter is configured to transmit the second radiation portion and to absorb or to reflect the remaining portion of the radiation; and
the reference detector filter is configured to absorb or to reflect the first radiation portion and the second radiation portion and to transmit at least the reference radiation portion.

9. A gas detection device in accordance with claim 1, wherein:
the reference photosensor comprises an InGaAs photosensor;

the second gas photosensor comprises an InGaAs photosensor; and the first gas photosensor comprises a type II semiconductor diode.

10. A gas detection device in accordance with claim 9, wherein the first gas photosensor comprises an InAsSb photosensor.

11. A gas detection device in accordance with claim 1, wherein the target gas comprises hydrocarbons.

12. A process comprising:
providing a gas detection device for monitoring an area for a target gas to be detected, the gas detection device comprising:
a radiation source configured to emit electromagnetic radiation such that at least a portion of the emitted radiation penetrates the area to be monitored;
a first gas photosensor configured to generate a first gas photosensor signal as a function of a first gas photosensor impinging electromagnetic radiation intensity;
a second gas photosensor configured to generate a second gas photosensor signal as a function of a second gas photosensor impinging electromagnetic radiation intensity;
a reference photosensor configured to generate a reference photosensor signal as a function of a reference photosensor impinging electromagnetic radiation intensity;
an array of filters, wherein the radiation source is configured to emit the electromagnetic radiation such that at least a portion of the emitted radiation impinges on the array of filters and the array of filters is configured to distribute impinging radiation as a function of wavelength onto the photosensors and the array of filters is configured and positioned in relation to the photosensors such that the distribution of impinging radiation, in a state with no gas attenuating the electromagnetic radiation present in the area to be monitored, comprises:
a first radiation portion in a predefined first wavelength range, which first radiation portion impinges on the first gas photosensor with an intensity above a predefined first radiation intensity limit and radiation outside of the first wavelength range does not impinge on the first gas photosensor or impinges on the first gas photosensor with an intensity below the predefined first radiation intensity limit,
a second radiation portion in a predefined second wavelength range, which second radiation portion impinges on the second gas photosensor with an intensity above a predefined second radiation intensity limit and radiation outside of the second wavelength range does not impinge on the second gas photosensor or impinges on the second gas photosensor with an intensity below the predefined second radiation intensity limit; and
a reference radiation portion in a predefined reference wavelength range, which reference radiation portion impinges on the reference photosensor with an intensity above a predefined reference radiation intensity limit, and radiation in the first wavelength range and radiation in the second wavelength range does not impinge on the reference photosensor or impinges on the reference photosensor with an intensity below the reference radiation intensity limit, wherein there is no overlap between two of the first wavelength range, the second wavelength range and the reference wavelength range; and
an analysis unit configured to compare the first gas photosensor signal, the second gas photosensor signal and the reference photosensor signal with one another based on the analysis unit being configured to: carry out a pair comparison for each of the first gas photosensor signal, the second gas photosensor signal and the reference photosensor signal comprising three pair comparisons of two photosensors including comparing the first gas photosensor signal with the second gas photosensor signal, comparing the second gas photosensor signal and the reference photosensor signal and comparing the first gas photosensor signal and the reference photosensor signal and as a function of the three pair comparison:
to determine whether or not the target gas to be detected is present in the area to be monitored; or
to determine a concentration indication of the target gas in the area to be monitored; or
to determine whether or not the target gas to be detected is present in the area to be monitored and to determine a concentration indication of the target gas in the area to be monitored; and
selecting the target gas to be detected and/or the first wavelength range, the second wavelength range and the reference wavelength range such that the target gas to be detected absorbs both emitted radiation in the first wavelength range and emitted radiation in the second wavelength range more intensely than the target gas to be detected absorbs emitted radiation in the reference wavelength range.

13. A process in accordance with claim 12, wherein the target gas comprises hydrocarbons.

14. A process in accordance with claim 12, wherein the target gas comprises at least one of methane, propane and ethylene.

15. A process for monitoring an area for a target gas to be detected, wherein the process is carried out using a gas detection device comprising a radiation source, a first gas photosensor, a second gas photosensor, a reference photosensor, an array of filters and an analysis unit, the process comprising the steps of:
emitting electromagnetic radiation into the area to be monitored with the radiation source such that at least a portion of the emitted electromagnetic radiation penetrates the area to be monitored and impinges on the array of filters;
distributing impinging radiation, as a function of the wavelength, onto the photosensors with the array of filters;
generating a first gas photosensor signal as a function of an intensity of impinging electromagnetic radiation on the first gas photosensor;
generating a second gas photosensor signal as a function of an intensity of impinging electromagnetic radiation on the second gas photosensor;
generating a reference gas photosensor signal as a function of an intensity of impinging electromagnetic radiation on the reference gas photosensor;
distributing impinging radiation with the array of filters such that in a state with no gas, which attenuates electromagnetic radiation being present in the area to be monitored:
a first radiation portion, in a predefined first wavelength range, impinges on the first gas photosensor with an intensity above a predefined first radiation intensity limit and radiation outside of the first wavelength range does not impinge on the first gas photosensor or does so with an intensity below the predefined first radiation intensity limit;

a second radiation portion, in a predefined second wavelength range, impinges on the second gas photosensor with an intensity above a predefined second radiation intensity limit and radiation outside of the second wavelength range does not impinge on the second gas photosensor or does so with an intensity below the predefined second radiation intensity limit;

a reference radiation portion, in a predefined reference wavelength range, impinges on the reference photosensor with an intensity above a predefined reference radiation intensity limit and radiation in the first wavelength range and radiation in the second wavelength range do not impinge on the reference photosensor or do so with an intensity below the predefined reference radiation intensity limit, wherein two of these respective three wavelength ranges do not overlap;

carrying out a comparison for each of the first gas photosensor signal, the second gas photosensor signal and the reference first gas photosensor signal with the analysis unit, the comparison comprising three pair comparisons of two photosensors including comparing the first gas photosensor signal with the second gas photosensor signal, comparing the second gas photosensor signal and the reference photosensor signal and comparing the first gas photosensor signal and the reference photosensor signal;

with the analysis unit, as a function of the result of the three pair comparison, determining whether or not the target gas to be detected is present in the area to be monitored or determining an indicator of a concentration of the target gas in the area to be monitored or determining whether or not the target gas to be detected is present in the area to be monitored and determining an indicator of a concentration of the target gas in the area to be monitored.

16. A process in accordance with claim 15, wherein:
the step of comparing comprises the analysis unit carrying out a pair comparison for each of the first gas photosensor signal, the second gas photosensor signal and the reference photosensor signal, wherein the pair comparison comprises three pair comparisons of two photosensors including comparing the first gas photosensor signal with the second gas photosensor signal, comparing the second gas photosensor signal and the reference photosensor signal and comparing the first gas photosensor signal and the reference photosensor signal; and
the step of determining comprises the analysis unit determining whether or not the target gas to be detected is present in the area to be monitored as a function of a result of the three pair comparisons.

17. A process in accordance with claim 16, wherein:
a reference comparison result is predefined, wherein the reference comparison result describes an expected comparison result in case of a state free from a gas which attenuates electromagnetic radiation; and
the analysis unit determines that the target gas is present, when the signal from the first gas photosensor and/or the signal from the second gas photosensor is attenuated more intensely than during the reference comparison result in relation to the signal from the reference photosensor.

18. A process in accordance with claim 15, wherein:
a reference comparison result is predefined, wherein the reference comparison result describes an expected comparison result in case of a state free from a gas which attenuates electromagnetic radiation; and
the analysis unit determines that the target gas is present, when the signal from the first gas photosensor and/or the signal from the second gas photosensor is attenuated more intensely than during the reference comparison result in relation to the signal from the reference photosensor.

19. A process in accordance with claim 15, wherein the target gas comprises hydrocarbons.

20. A process in accordance with claim 15, wherein the target gas comprises at least one of methane, propane and ethylene.

21. A gas detection device for monitoring an area for a target gas to be detected, the gas detection device comprising:
a radiation source configured to emit electromagnetic radiation such that at least a portion of the emitted radiation penetrates the area to be monitored;
a first gas photosensor configured to generate a first gas photosensor signal as a function of a first gas photosensor impinging electromagnetic radiation intensity;
a second gas photosensor configured to generate a second gas photosensor signal as a function of a second gas photosensor impinging electromagnetic radiation intensity;
a reference photosensor configured to generate a reference photosensor signal as a function of a reference photosensor impinging electromagnetic radiation intensity;
an array of filters, wherein the radiation source is configured to emit the electromagnetic radiation such that at least a portion of the emitted radiation impinges on the array of filters and the array of filters is configured to distribute impinging radiation as a function of wavelength onto the photosensors and the array of filters is configured and positioned in relation to the photosensors such that the distribution of impinging radiation, in a state with no gas attenuating the electromagnetic radiation present in the area to be monitored, comprises:
a first radiation portion in a predefined first wavelength range, which first radiation portion impinges on the first gas photosensor with an intensity above a predefined first radiation intensity limit and radiation outside of the first wavelength range does not impinge on the first gas photosensor or impinges on the first gas photosensor with an intensity below the predefined first radiation intensity limit,
a second radiation portion in a predefined second wavelength range, which second radiation portion impinges on the second gas photosensor with an intensity above a predefined second radiation intensity limit and radiation outside of the second wavelength range does not impinge on the second gas photosensor or impinges on the second gas photosensor with an intensity below the predefined second radiation intensity limit; and
a reference radiation portion in a predefined reference wavelength range, which reference radiation portion impinges on the reference photosensor with an intensity above a predefined reference radiation intensity limit, and radiation in the first wavelength range and radiation in the second wavelength range does not impinge on the reference photosensor or impinges on the reference photosensor with an intensity below the reference radiation intensity limit, wherein there is no overlap between two of the first wavelength range, the second wavelength range and the reference wavelength range; and an analysis unit configured to compare the first gas photosensor signal, the second gas photosensor signal and the reference photosensor signal with one another and as a function of the comparison:
  to determine whether or not the target gas to be detected is present in the area to be monitored; or
  to determine a concentration indication of the target gas in the area to be monitored; or
  to determine whether or not the target gas to be detected is present in the area to be monitored and to determine a concentration indication of the target gas in the area to be monitored, wherein the array of filters comprises a first optical filter and a second optical filter, the first optical filter is configured to reflect electromagnetic radiation in the first wavelength range and to transmit electromagnetic radiation outside of the first wavelength range, and radiation reflected by the first optical filter impinges on the first gas photosensor and radiation transmitted by the first optical filter impinges on the second optical filter; and wherein:
  the second optical filter is configured to transmit electromagnetic radiation in the second wavelength range and to reflect electromagnetic radiation outside of the second wavelength range and radiation reflected by the second optical filter impinges on the reference photosensor and radiation transmitted by the second optical filter impinges on the second gas photosensor; or
  the second optical filter is configured to reflect electromagnetic radiation in the second wavelength range and to transmit electromagnetic radiation outside of the second wavelength range, and radiation transmitted by the second optical filter impinges on the reference photosensor and radiation reflected by the second optical filter impinges on the second gas photosensor.

* * * * *